(12) United States Patent
Daggett et al.

(10) Patent No.: US 8,242,241 B2
(45) Date of Patent: Aug. 14, 2012

(54) COMPUTATIONALLY DESIGNED INHIBITORS OF AMYLOIDOSIS

(75) Inventors: Valerie Daggett, Woodinville, WA (US); Peter Law, Seattle, WA (US)

(73) Assignee: University of Washington, Seattle, WA (US)

( * ) Notice: Subject to any disclaimer, the term of this patent is extended or adjusted under 35 U.S.C. 154(b) by 859 days.

(21) Appl. No.: 12/079,947

(22) Filed: Mar. 27, 2008

(65) Prior Publication Data
US 2009/0248379 A1 Oct. 1, 2009

(51) Int. Cl.
*A61K 38/16* (2006.01)
(52) U.S. Cl. .................. 530/326; 514/21.4
(58) Field of Classification Search .......... None
See application file for complete search history.

(56) References Cited

OTHER PUBLICATIONS

Armen, R.S. et all. "Characterization of two distinct beta2-microglobulin unfolding intermediates that may lead to amyloid fibrils of different morphology", Biochemistry, 2005, vol. 44, No. 49, Abstract Only.

Armen, R.S. et al., "Characterization of a possible amyloidogenic precursor in glutamine-repeat neurodegenerative diseases", Proc. Natl. Acad. Sci., 2005, vol. 102, No. 38, pp. 13433-13438.
Daggett, V., "Alpha-sheet: The toxic conformer in amyloid diseases?", Acc. Chem. Res., 2006, vol. 39, No. 9, Abstract Only.
Demarco, M.L. et al., "Structural properties of prion protofibrils and fibrils: an experimental assessment of atomic models", Biochemistry, 2006, vol. 45, pp. 15573-15582.

*Primary Examiner* — Christina Bradley
(74) *Attorney, Agent, or Firm* — McDonnell Boehnen Hulbert & Berghoff LLP

(57) ABSTRACT

Embodiments of the present invention include methods and systems for designing inhibitors of amyloidosis in humans, domesticated animals, and wild animals as well as inhibitors of amyloidosis designed by the methods and systems. Methods and systems for designing inhibitors of amyloidosis are largely computational, in nature, and are directed to designing various types of polymers, small-molecule organic compounds, organometallic compounds, or non-chemical physical processes that can target the extended-α-strand and α-sheet regions of amyloidogenic protein and polypeptide intermediates in order to prevent aggregation of those intermediates into protofibrils and fibrils that, in turn, recruit additional native-conformation proteins and polypeptides into amyloidogenic intermediates and that additionally aggregate to form higher-order structures, such as plaques observed in the brains of patients suffering from the various spongiform encephalopathies.

4 Claims, 39 Drawing Sheets

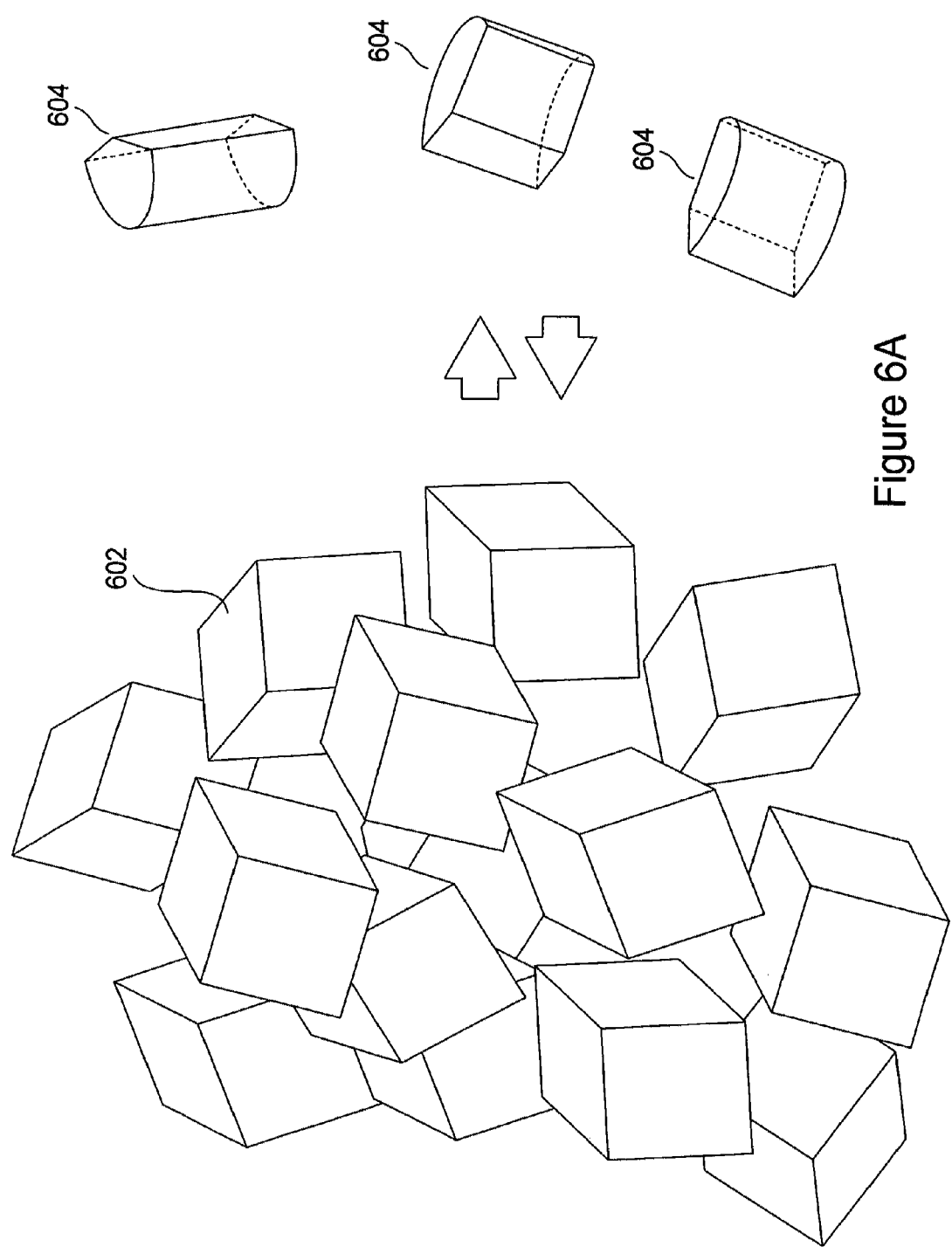

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: optional L isomer
<220> FEATURE:
<221> NAME/KEY: MISC_FEATURE
<222> LOCATION: (4)..(4)
```

-continued

```
<223> OTHER INFORMATION: optional D isomer
<220> FEATURE:
<221> NAME/KEY: MISC_FEATURE
<222> LOCATION: (5)..(5)
<223> OTHER INFORMATION: optional L isomer
<220> FEATURE:
<221> NAME/KEY: MISC_FEATURE
<222> LOCATION: (6)..(6)
<223> OTHER INFORMATION: optional D isomer
<220> FEATURE:
<221> NAME/KEY: MISC_FEATURE
<222> LOCATION: (7)..(7)
<223> OTHER INFORMATION: optional L isomer
<220> FEATURE:
<221> NAME/KEY: MISC_FEATURE
<222> LOCATION: (8)..(8)
<223> OTHER INFORMATION: optional D isomer
<220> FEATURE:
<221> NAME/KEY: MISC_FEATURE
<222> LOCATION: (9)..(15)
<223> OTHER INFORMATION: optional L isomer
<220> FEATURE:
<221> NAME/KEY: MISC_FEATURE
<222> LOCATION: (16)..(16)
<223> OTHER INFORMATION: optional D isomer
<220> FEATURE:
<221> NAME/KEY: MISC_FEATURE
<222> LOCATION: (17)..(17)
<223> OTHER INFORMATION: optional L isomer
<220> FEATURE:
<221> NAME/KEY: MISC_FEATURE
<222> LOCATION: (18)..(18)
<223> OTHER INFORMATION: optional D isomer
<220> FEATURE:
<221> NAME/KEY: MISC_FEATURE
<222> LOCATION: (19)..(19)
<223> OTHER INFORMATION: optional L isomer
<220> FEATURE:
<221> NAME/KEY: MISC_FEATURE
<222> LOCATION: (20)..(20)
<223> OTHER INFORMATION: optional D isomer
<220> FEATURE:
<221> NAME/KEY: MISC_FEATURE
<222> LOCATION: (21)..(23)
<223> OTHER INFORMATION: optional L isomer

<400> SEQUENCE: 1

Arg Gly Glu Met Asn Leu Ser Trp Met Asn Glu Tyr Ser Gly Trp Thr
1               5                   10                  15

Met Asn Leu Lys Met Gly Arg
            20
```

US 8,242,241 B2

COMPUTATIONALLY DESIGNED INHIBITORS OF AMYLOIDOSIS

STATEMENT OF GOVERNMENT INTEREST

This invention was made with government support under 5R01-GM050789-13 awarded by the National Institutes of Health. The government has certain rights in the invention.

TECHNICAL FIELD

The present invention is related to the design and development of therapeutics and therapies for treating various amyloid diseases and pathologies, including transmissible spongiform encephalopathies, such as Creutzfeldt-Jakob disease, Huntington's disease and amyotrophic lateral sclerosis, senile systemic amyloidosis, and familial amyloid polyneuropathy and, in particular, to inhibitors of amyloidosis and to a method and system for computationally designing inhibitors of amyloidosis that prevent or ameliorate various amyloid diseases.

BACKGROUND OF THE INVENTION

Currently, 25 different human amyloid diseases are known. These diseases include Creutzfeldt-Jakob disease, one of a number of transmissible spongiform encephalopathies, Huntington's disease, amyotrophic lateral sclerosis, senile systemic amyloidosis, familial amyloid polyneuropathy, Kennedy disease, and Machado-Joseph Disease. Amyloidosis is characterized by aggregation of proteins and/or peptides, and each different amyloid disease appears to result from partial unfolding and refolding of a particular protein or peptide into an amyloidogenic intermediate, such as the partial unfolding and refolding of the well-known prion protein $PrP^C$ into the amyloidogenic intermediate $PrP^{SC}$, which then aggregates to form larger structures, including fibrils and deposits. Molecular dynamics ("MD") computational simulations of native-conformation and amyloidogenic-intermediate proteins and peptides have revealed that many of the amyloidogenic-intermediate proteins and peptides exhibit an unusual secondary structure referred to as α-sheet, described in a subsequent section of this document. It has been proposed that regions of α-sheet or extended α-strand within amyloidogenic intermediates provide inter-protein or inter-polypeptide binding sites that allow the soluble amyloidogenic intermediates to aggregate into polymer-like protofibrils and fibrils, which can, in turn, then aggregate into larger, insoluble structures, such as the plaques observed in the brain tissue of patients suffering from various spongiform encephalopathies. The extended-α-strand secondary structure has been only rarely observed in non-amyloidogenic protein structures, and α-sheet secondary structure has not been observed in non-amyloidogenic protein structures, but MD simulations have revealed extended-α-strand and α-sheet secondary structure in those amyloidogenic intermediates so far studied. As discussed below, the extended-α-strand and α-sheet secondary structure features an uncharacteristic dipole moment approximately orthogonal to the polypeptide backbone and features extended chains of carbonyl oxygens, on one side, and amide hydrogens, on the opposite side, both excellent targets for hydrogen bonding. The α-strand and α-sheet secondary structure may be only transiently exhibited during the amyloidosis process, amyloidogenic intermediates, and may transform to β-pleated sheet or other secondary-structure motifs as the conformation of protein and polypeptide monomers within higher-order aggregates, including fibrils and plaques, changes to more stable conformations within the higher-order aggregates.

Human amyloid diseases currently account for annual expenditure of over $100 billion in health care costs, and these costs are rising as more human amyloid diseases are clinically recognized. The costs of caring for those suffering from amyloid diseases may significantly rise with increasing rates of transmission of the transmissible forms of amyloidogenic intermediates, such as the infective prion protein $PrP^{SC}$. Currently, there are no effective treatments or therapies for amyloid diseases, and the toll in human lives and in the disruptions in lives of family members, care-givers, and employers of those afflicted with amyloid disease is incalculable. Medical and scientific researchers, health care providers, government agencies, and, ultimately, those susceptible to amyloid diseases and those who care for victims of amyloid diseases have all recognized the need for medical therapies for preventing and/or ameliorating amyloid diseases in the human population. The serious impact of amyloid diseases on populations of domesticated and wild animals is also recognized as an enormous problem for which palliative or curative veterinary pharmaceuticals are desperately needed.

SUMMARY OF THE INVENTION

Embodiments of the present invention include methods and systems for designing inhibitors of amyloidosis in humans, domesticated animals, and wild animals as well as inhibitors of amyloidosis designed by the methods and systems. Methods and systems for designing inhibitors of amyloidosis are largely computational, in nature, and are directed to designing various types of polymers, small-molecule organic compounds, organometallic compounds, or non-chemical physical processes that can target the extended-α-strand and α-sheet regions of amyloidogenic protein and polypeptide intermediates in order to prevent aggregation of those intermediates into protofibrils and fibrils that, in turn, recruit additional native-conformation proteins and polypeptides into amyloidogenic intermediates and that additionally aggregate to form higher-order structures, such as plaques observed in the brains of patients suffering from the various spongiform encephalopathies.

BRIEF DESCRIPTION OF THE DRAWINGS

FIGS. 6A-D illustrate a generalized sequence of steps by which polypeptides and proteins conformationally change and aggregate together to form higher-order structures.

DETAILED DESCRIPTION OF THE INVENTION

Embodiments of the present invention are directed to computational methods for designing inhibitors of amyloidosis, to small-molecule and polymer amyloidosis inhibitors designed by these computational methods, and even to any of various non-chemical physical processes that may be designed to inhibit computationally derived binding sites at which amyloidogenic intermediates bind together to form polymer-like aggregates. Discussion of the method, system, and therapeutic embodiments of the present invention follows a number of initial subsections, below, that provide overviews of: (1) protein and protein structure, including extended α-strand and α-sheet; (2) the process by which certain proteins and polypeptides unfold and refold to produce amyloidogenic precursors and subsequently aggregate to form protofibrils, fibrils, and higher-order structures; and (3) other aspects of amyloid diseases.

Overview of Polypeptides and Proteins

Figures 1A, 1B:
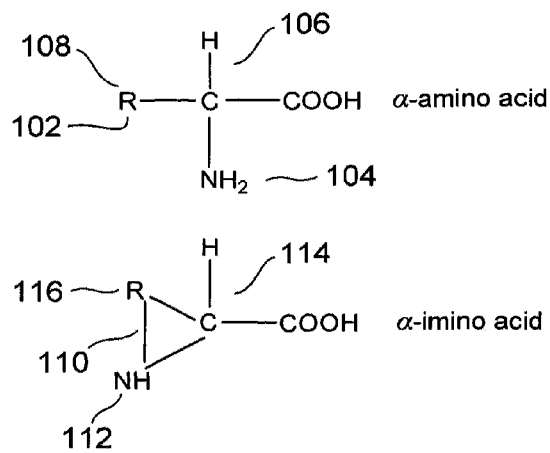
FIG. 1A shows the general structure of an α-amino acid and an α-imino acid.
FIG. 1B provides a table of the common α-amino acids and α-imino acid.

Naturally occurring polypeptides and proteins are, for the most part, polymers of 19 common amino acids and one common imino acid. FIG. 1A shows the general structure of an α-amino acid and an α-imino acid. An α-amino acid is a carboxylic acid 102 with an amino substituent 104 at the α-carbon position 106 of the carboxylic acid. Each of the 19 common α-amino acids have this general structure, and differ from one another by having different R-group substituents 108 at the α-carbon position 106. An α-imino acid 110 has a similar structure, except that the α-imino nitrogen 112 is covalently bound both to the α carbon 114 and to the R-group substituent 116 of the α carbon.

FIG. 1B provides a table of the common α-amino acids and α-imino acid. This table includes two three-column listings of the common α-amino acids and α-imino acid. Each three-column listing 120 and 122 provides the structure of the R-group 124 and 126, the name of the α-amino or α-imino acid 128 and 130, and a single-character abbreviation for the α-amino or α-imino acid 132 and 134. The single α-imino acid is named "proline" 136. Certain of the α-amino acids have non-polar, aliphatic, hydrophobic R groups, such as valine 138. Other of the α-amino acids have acidic, generally negatively charged R groups, such as aspartic acid 140 and glutamic acid 142, or basic, generally positively charged R groups, such as arginine 144 and lysine 145. Other amino acids feature hydroxyl, sulfydryl, and aromatic side groups. In addition to the common α-amino and α-imino acids listed in FIG. 1B, naturally occurring peptides and proteins may additionally contain various derivatives of these α-amino acids as well as various unusual, infrequently encountered amino acids.

Figure 1C:
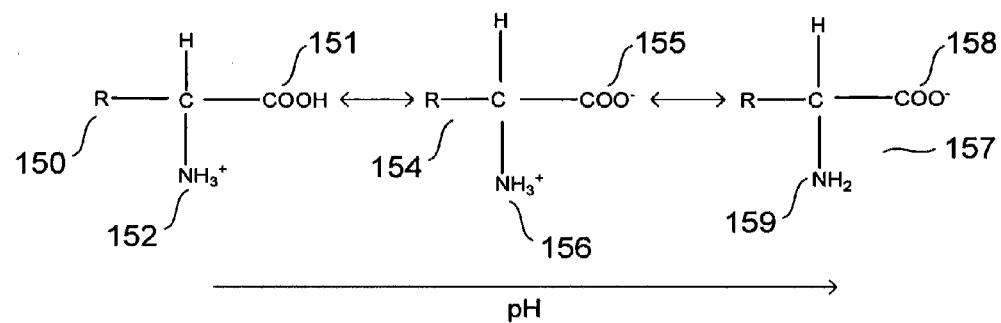
FIG. 1C shows three different ionic forms of an amino acid that may exist alone or in combination in solutions of different pH.

In solution, an amino acid may have any of various different ionic forms. FIG. 1C shows three different ionic forms of an amino acid that may exist alone or in combination in solutions of different pH. At low pH, a positively charged ionic form 150 predominates, in which both the carboxylic-acid group 151 and amino group 152 are protonated. At an intermediate pH, a Zwitterionic form 154 predominates, in which the carboxylic acid 155 is deprotonated while the amino group 156 remains protonated. At high pH, a negatively charged ionic form 157 predominates in which the carboxylic acid group 158 and amino group 159 are both deprotonated. Of course, a particular amino acid may have additional ionic forms, when the R group contains additional acidic or basic substituents. For example, the R group of lysine (145 in FIG. 1B) includes an amino group that is protonated at low pH and intermediate pH and deprotonated at high pH.

Figure 1E:
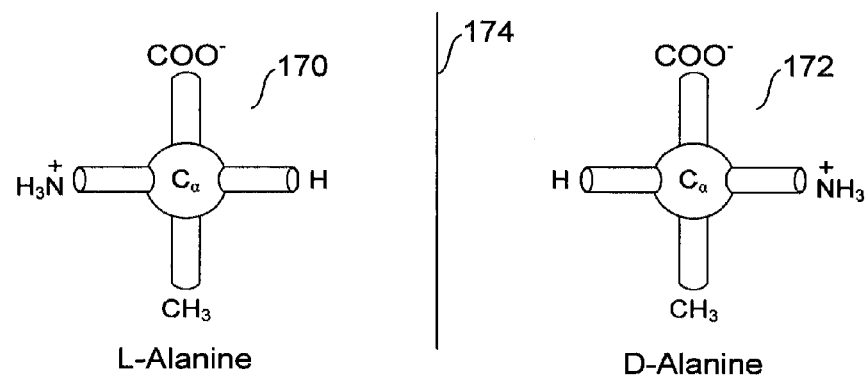
FIG. 1E illustrates the conformations of two different possible stereoisomers of an amino acid with respect to the $C_\alpha$ position within the amino acid.
Figure 1D:
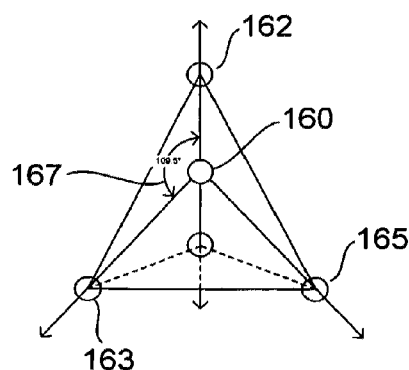
FIG. 1D illustrates the tetrahedral nature of a carbon atom covalently bound to four substituents.

FIG. 1D illustrates the tetrahedral nature of a carbon atom covalently bound to four substituents. In particular, the carbon atom at the α position within an amino acid (106 and 114 in FIG. 1A) 160 can be thought of as positioned within a regular tetrahedron, with substituents positioned at each vertex of the tetrahedron 162-165. As indicated in FIG. 1D by the curved arrow 167, the angle between any two bonds joining a substituent to the $C_\alpha$ carbon atom is 109.5°.

FIG. 1E illustrates the conformations of two different possible stereoisomers of an amino acid with respect to the $C_\alpha$ position within the amino acid. Because of the tetrahedral nature of the $C_\alpha$ atom, and because the $C_\alpha$ atom generally has four different, distinct substituents (except for glycine), amino acids, other than glycine, are stereoisomeric at the $C_\alpha$ position. As shown in FIG. 1E, the two stereoisomers 170 and 172 are related to one another by mirror-plane symmetry 174. In other words, reflection of one stereoisomer in a mirror generates the other stereoisomer. The L stereoisomer 170 is most frequently encountered in biological materials, and almost all naturally occurring proteins include only L stereoisomers of amino acids. The D stereoisomer 172 is observed in racemic mixtures obtained as the product of organic synthesis, when stereoisometry is not controlled by reaction conditions, and is occasionally encountered in biological materials such as cyclic peptide antibacterials and ionophors.

Figure 2A:
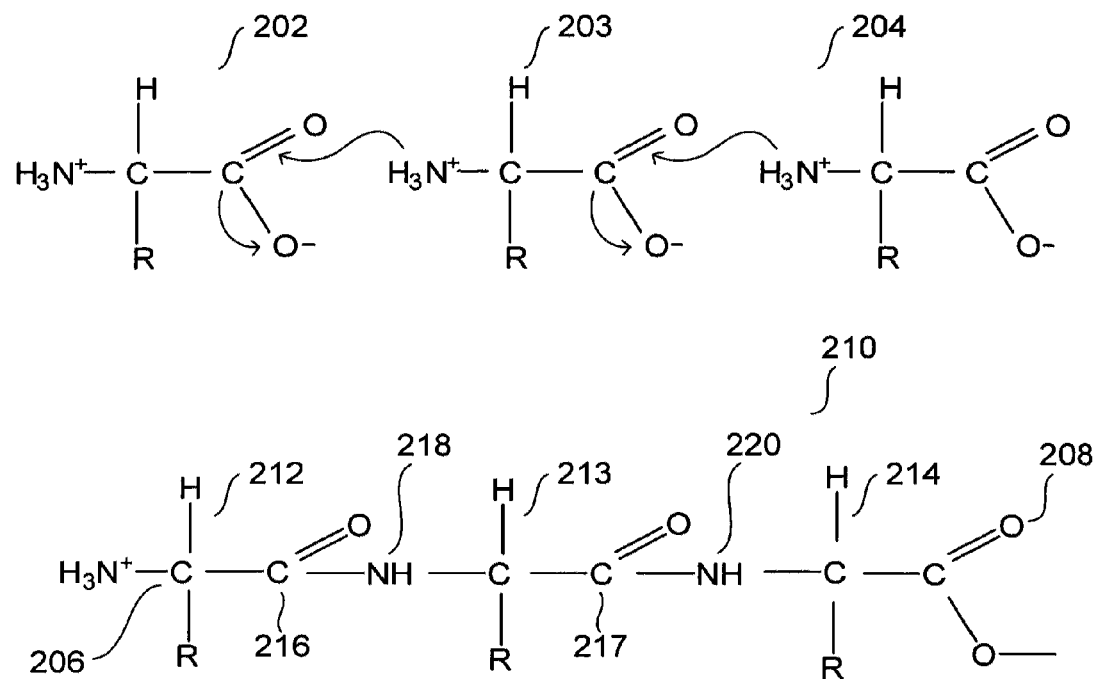
FIG. 2A illustrates polymerization of three amino acids to form a polypeptide.

FIG. 2A illustrates polymerization of three amino acids to form a polypeptide. Amino acids 202-204 can, under proper conditions, undergo a condensation reaction by which the amine nitrogen on a first amino acid displaces a carboxylic-acid-group oxygen on a second amino acid to form an amide bond. Thus, amino acids are monomers within polypeptide polymers. In biological organisms, most polypeptides are synthesized by a ribosome-and-tRNA-mediated mRNA translation process. Proteins are large biopolymers consisting of one or more separate polypeptide chains. Normally, polypeptide sequences are written with the free-amino-group containing amino acid 206 on the left-hand side and the free-carboxylic-acid-containing amino acid 208 on the right-hand side. The polypeptide backbone consists of repeating 3-atom sequences that each includes a $C_\alpha$ atom, a carbonyl-carbon atom, and an amide nitrogen atom, and is generally represented as a linear, horizontal sequence, although, as discussed below, the backbone conformation is actually non-linear. Thus, in the three-amino-acid polypeptide 210 shown in FIG. 2A, the polypeptide backbone comprises $C_\alpha$ carbons 212-214, carbonyl carbons 216 and 217, and amide nitrogens 218 and 220. Polypeptide structures are generally written with R-group substituents vertically displaced from the $C_\alpha$ carbons, although that convention does not reflect actual spatial directions of the bonds or spatial positions of the atoms.

Figure 2B:
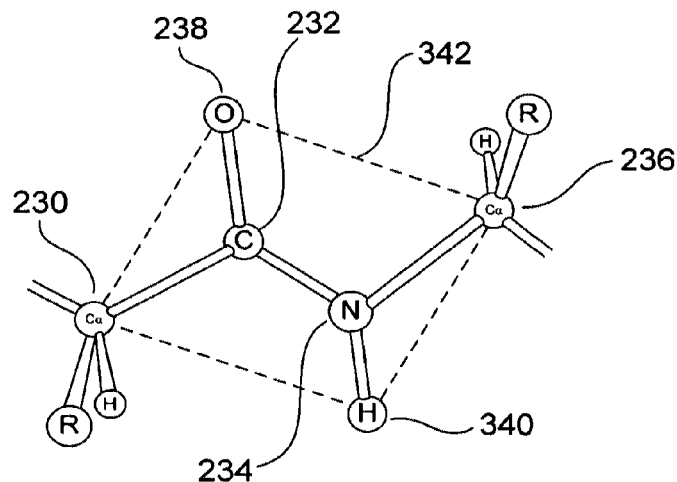
FIG. 2B shows a planar arrangement of four background atoms and two substituents of background atoms within a polypeptide polymer.
Figure 2C:
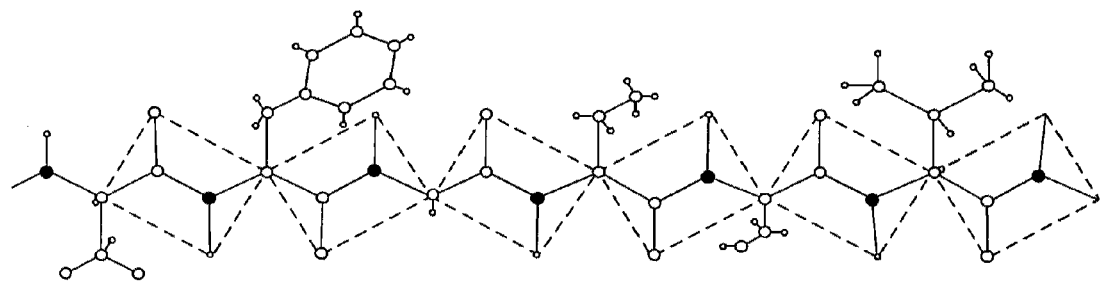
FIG. 2C shows planar arrangements of atoms along a polypeptide chain.

FIG. 2B shows a planar arrangement of four background atoms and two substituents of background atoms within a polypeptide polymer. FIG. 2B shows a short stretch of a polypeptide-backbone structure beginning with a first $C_\alpha$ atom 230 and extending through a carbonyl carbon 232 and amide nitrogen 234 to a second $C_\alpha$ atom 236. Because of delocalization of π electrons of the carbonyl group over the amide bond, the four backbone atoms shown in FIG. 2B, along with the carbonyl oxygen 238 and amide hydrogen 240, are all approximately planar, and located within the plane described by dashed lines 242 in FIG. 2B. FIG. 2C shows planar arrangements of atoms along a polypeptide chain using the same dashed-line convention as used in FIG. 2B.

Figure 2D:
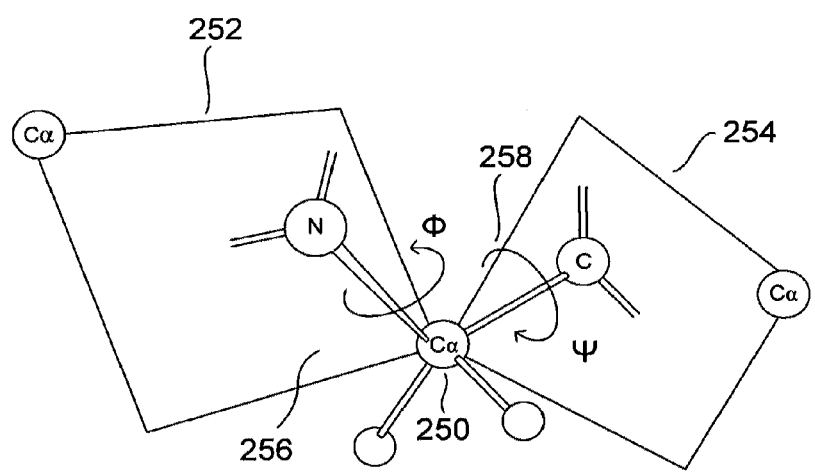
FIG. 2D illustrates Φ and Ψ torsion angles.

FIG. 2D illustrates Φ and Ψ torsion angles. Because of the planar arrangement of many of the backbone atoms, as shown in FIG. 2C, the conformation of a polypeptide backbone is fully specified by two torsion angles with respect to each $C_\alpha$ carbon in the polypeptide backbone. As shown in FIG. 2D, each $C_\alpha$ carbon 250 lies at the vertices of two different planar regions 252 and 254. The torsion angle Φ 256 about the amide bond and the torsion angle Ψ 258 about the $C_\alpha$— carbonyl-carbon bond describe all possible arrangements of the adjacent planar regions with respect to the $C_\alpha$ bond 250 lying at vertices of both planar regions. By specifying the Φ and Ψ torsion angles for each $C_\alpha$ along a polypeptide backbone, any possible polypeptide-backbone conformations can be fully specified.

Figure 3:
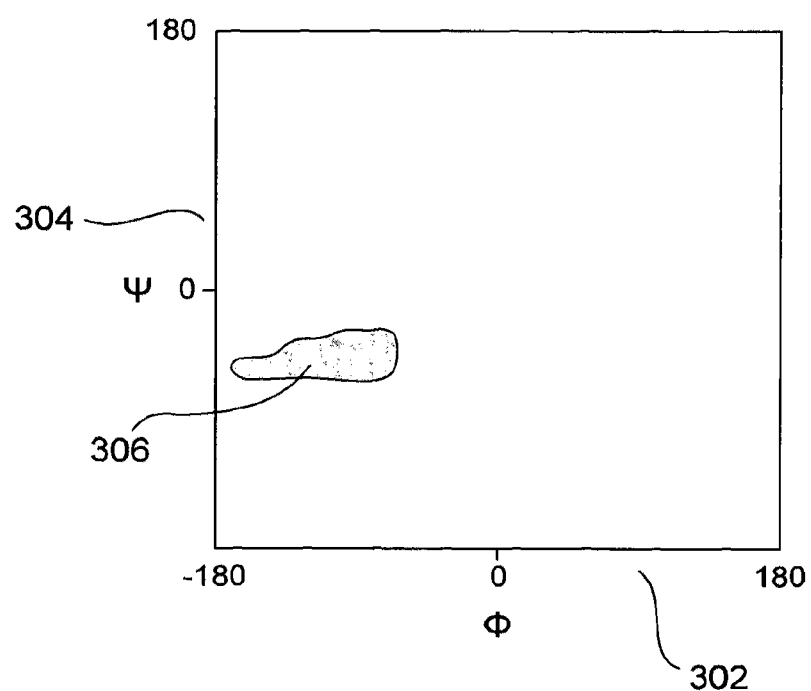
FIG. 3 shows a Ramachandran plot of Φ/Ψ torsion angles for each $C_\alpha$ carbon in a right-handed α helix.

Polypeptides and proteins are generally not linear structures, but are instead folded into elaborate three-dimensional structures that often contain regions of well-defined secondary structure. Two commonly encountered types of secondary structure are α helices and β-pleated sheets. These regular, secondary-structure conformations of polypeptides can be described as a constraining of the Φ and Ψ torsion angles along the polypeptide chain to narrow ranges of values. FIG. 3 shows a Ramachandran plot of Φ/Ψ torsion angles for each $C_\alpha$ carbon in a right-handed α helix. The Φ angles are plotted with respect to a Φ axis 302 and the Ψ angles are plotted with respect to a Ψ axis 304. For a right-handed α-helix, the possible Φ/Ψ angle pairs for each $C_\alpha$ carbon fall within a small region 306 of the area of the Ramachandran plot representing all possible Φ/Ψ angle pairs.

Figure 4:
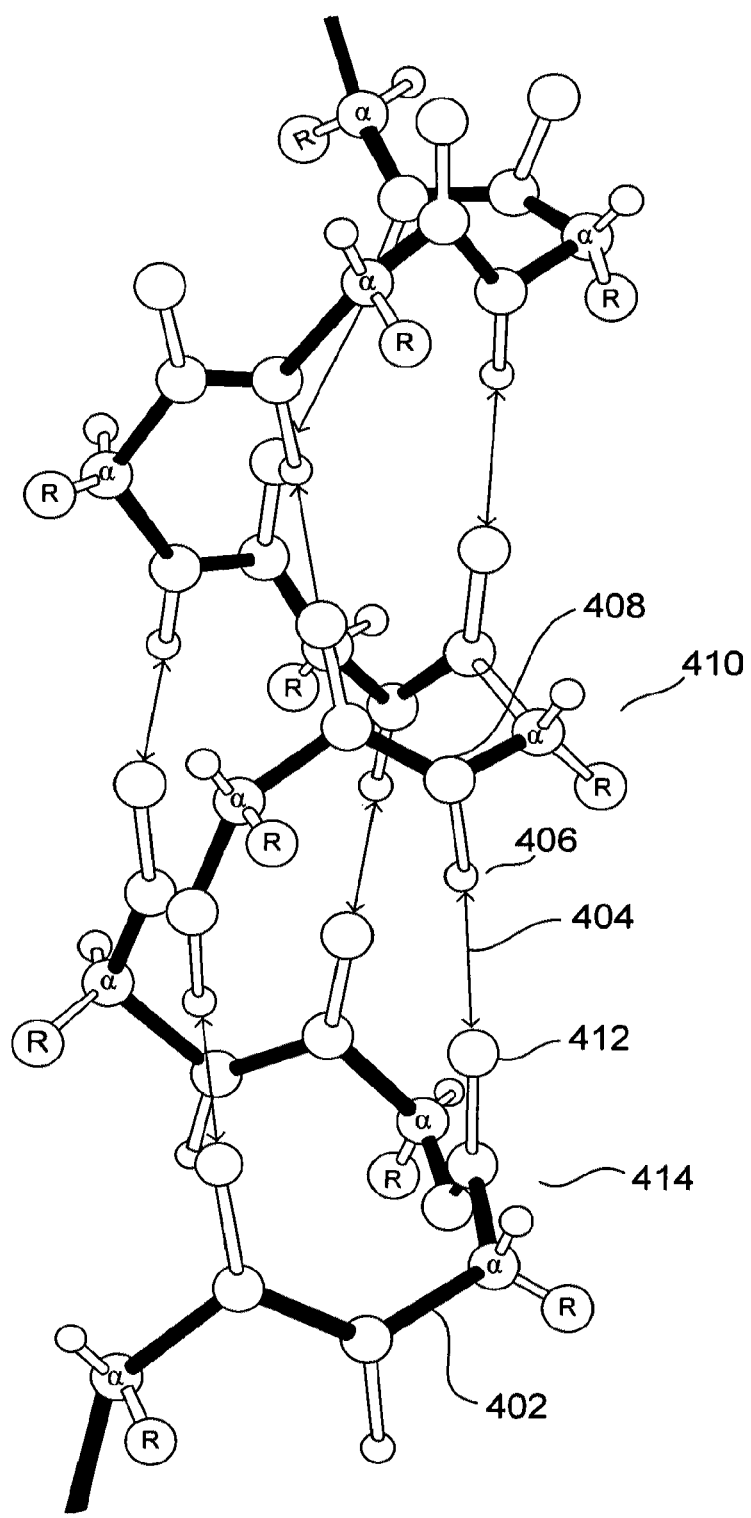
FIG. 4 illustrates a small section of right-handed α helix.

FIG. 4 illustrates a small section of right-handed α helix. In FIG. 4, the backbone bonds, such as bond 402, are shaded to prominently display the helix formed by the polypeptide backbone about an approximately vertical axis. The helix structure is stabilized by hydrogen bonds, indicated in FIG. 4 by double-headed arrows, such as hydrogen bond 404. Each hydrogen bond is a weak electrostatic bond in which an amide hydrogen is shared between the weakly acidic amide and a weakly basic carbonyl oxygen. In the α-helix structure, the amide hydrogen 406 is covalently bound to an amide nitrogen 408 of a first amino-acid monomer 410, and the amide hydrogen 406 is shared with the carbonyl oxygen 412 of a second amino-acid residue 414 displaced by four residues from the first amino acid along the polypeptide backbone.

Figure 5:
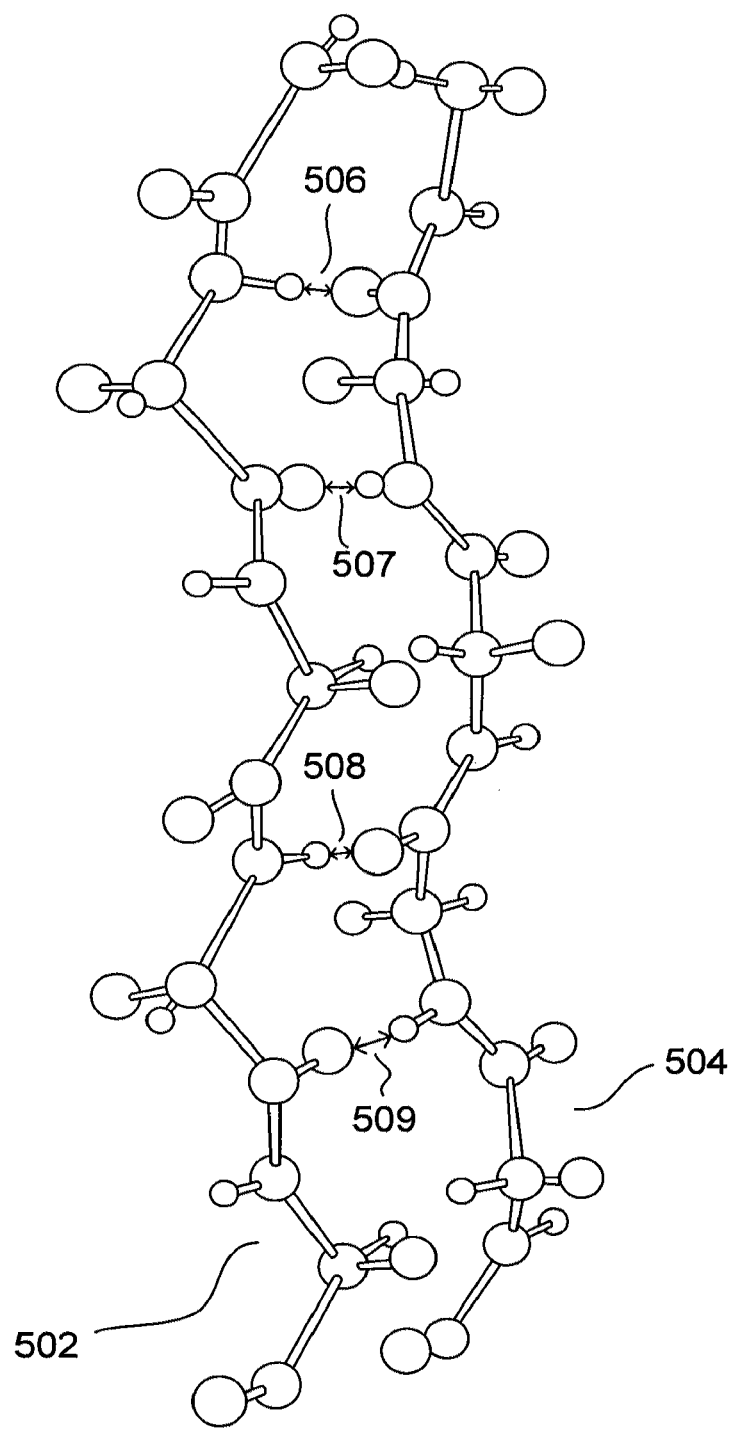
FIG. 5 illustrates a small region of β-pleated-sheet secondary structure.

FIG. 5 illustrates a small region of β-pleated-sheet secondary structure. In FIG. 5, two polypeptide strands 502 and 504 are laterally displaced from one another, and held in a stable, roughly parallel arrangement by inter-strand hydrogen bonds 506-509. The polypeptide strands may be two portions of a single polypeptide chain, or may be portions of two different polypeptide chains. The β-pleated-sheet motif can be extended laterally to produce a pleated-sheet-like structure. Note that, along each strand of the β-pleated-sheet structure, carbonyl oxygens are alternately displaced toward the opposite strand and away from the opposite strand. Carbonyl bonds have significant dipole moments, but because the carbonyl bonds alternate in direction by approximately 180°, the dipole moments tend to cancel one-another over the length and width of the β-pleated-sheet structure.

Many other different types of structural motifs, characterized by Φ/Ψ constraints, can be found within complex three-dimensional structures of proteins. The three-dimensional structure of proteins is generally quite complex, and determined by many different types of forces and thermodynamic properties, including hydrophobic interactions, solvation, hydrogen bonds, ionic interactions between side chains (R groups) covalent bonds between side chains. The various types of protein functions are partially or fully determined by the three-dimensional structures of proteins, including the shapes, sizes, and arrangement of catalytic groups within catalytic domains of enzymes.

Amyloidosis

Amyloidosis is the process by which certain polypeptides and proteins that presumably play various, useful roles in an organism conformationally change to become amyloidogenic intermediates which then aggregate together to form higher-order aggregates. Amyloidosis thus involves only conformational changes, or at least appears to involve only conformational changes in the transformation of the native-conformation protein or polypeptide, referred to below as the "amyloidogenic precursor protein" or "amyloidogenic precursor polypeptide," to amyloidogenic intermediate. Amyloidogenic-precursor proteins that can generate amyloidogenic intermediates include prion, lysozyme, transthyretin, $\beta_2$-microglobulin and polyglutamine.

Figure 6B:
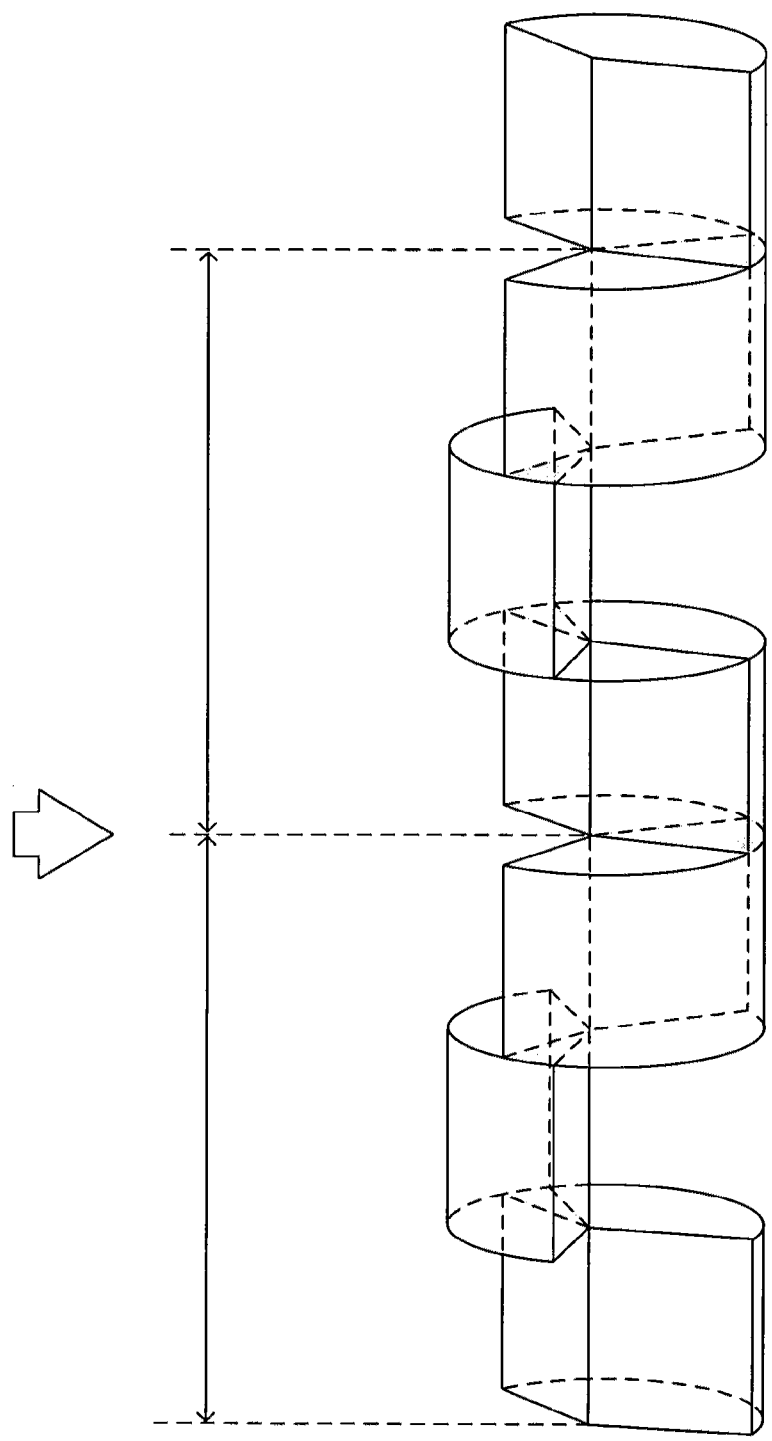

FIGS. 6A-D illustrate a generalized sequence of steps by which polypeptides and proteins conformationally change and aggregate together to form higher-order structures. While the sequence of steps shown in FIG. 6A-D is drawn from results of research on the prion protein $PrP^C$ and amyloid plaques observed in patients with various types of spongiform encephalopathies, similar aggregation pathways underlie most amyloid diseases. As shown in FIG. 6A, there may be an equilibrium between the normal, native conformation of an amyloidogenic precursor protein, represented in FIG. 6A by parallelepiped objects, such as parallelepiped 602, and the conformation of the amyloidogenic intermediate 604 that is formed by partial unfolding and refolding of the amyloidogenic precursor protein or polypeptide. In general, the equilibrium constant, expressed as the ratio of the equilibrium concentration the amyloidogenic intermediate to the equilibrium concentration of the amyloidogenic precursor protein, which describes the equilibrium under particular solution conditions, including temperature, pH, and ionic strength, is extremely small. However, under certain conditions, including the low-pH environments of endocytotic vesicles, and the presence of one or more amyloidogenic intermediates, or protofibrils composed of amyloidogenic intermediates, the equilibrium constant may substantially increase, and is thus shifted in favor of the conformation of the amyloidogenic intermediate (604 in FIG. 6A). The $PrP^C$ protein contains primarily α-helices, while the $PrP^{Sc}$ protein contains primarily β-like extended secondary structure. The driving force and stabilization force for conformational transformation and aggregation are believed to be exposure of hydrophobic surfaces, electrostatic interactions, aromatic stacking, and main chain-main chain interactions.

For certain amyloidogenic precursor proteins, the equilibrium constant may be so small that no amyloidogenic intermediates would be expected to spontaneously arise, and the conformational transformation of amyloidogenic precursor protein to amyloidogenic intermediate occurs only through conformational recruitment by an amyloidogenic intermediate or amyloidogenic-intermediate containing protofibril of exogenous origin.

Because of the change of conformation from amyloidogenic-precursor protein to amyloidogenic intermediate, binding or docking sites appear, based on MD simulation, to form at or near the exterior surface of the amyloidogenic intermediates. Because of the presence of these binding or docking sites, the amyloidogenic intermediates aggregate together to form protofibrils, an example of which is schematically shown in FIG. 6B. The equilibrium constant between discrete amyloidogenic intermediates and protofibrils may so favor protofibril formation that protofibril formation is essentially an irreversible process. $PrP^{SC}$ amyloid intermediates appear to aggregate to form helical protofibrils, with three $PrP^{SC}$ proteins per turn of the helix, as shown in FIG. 6B. In other words, the protofibrils are thought to exhibit a $3_1$ screw-axis symmetry. Unfortunately, it has not been possible to crystallize the amyloid intermediates or higher-order aggregates, such as protofibrils and fibrils, and concentrated solutions of the amyloid intermediates cannot be prepared. Therefore, even low-medium three-dimensional structures, normally obtained by NMR or x-ray crystallography, are not available for amyloid intermediates or higher-order aggregates.

Figure 6C:
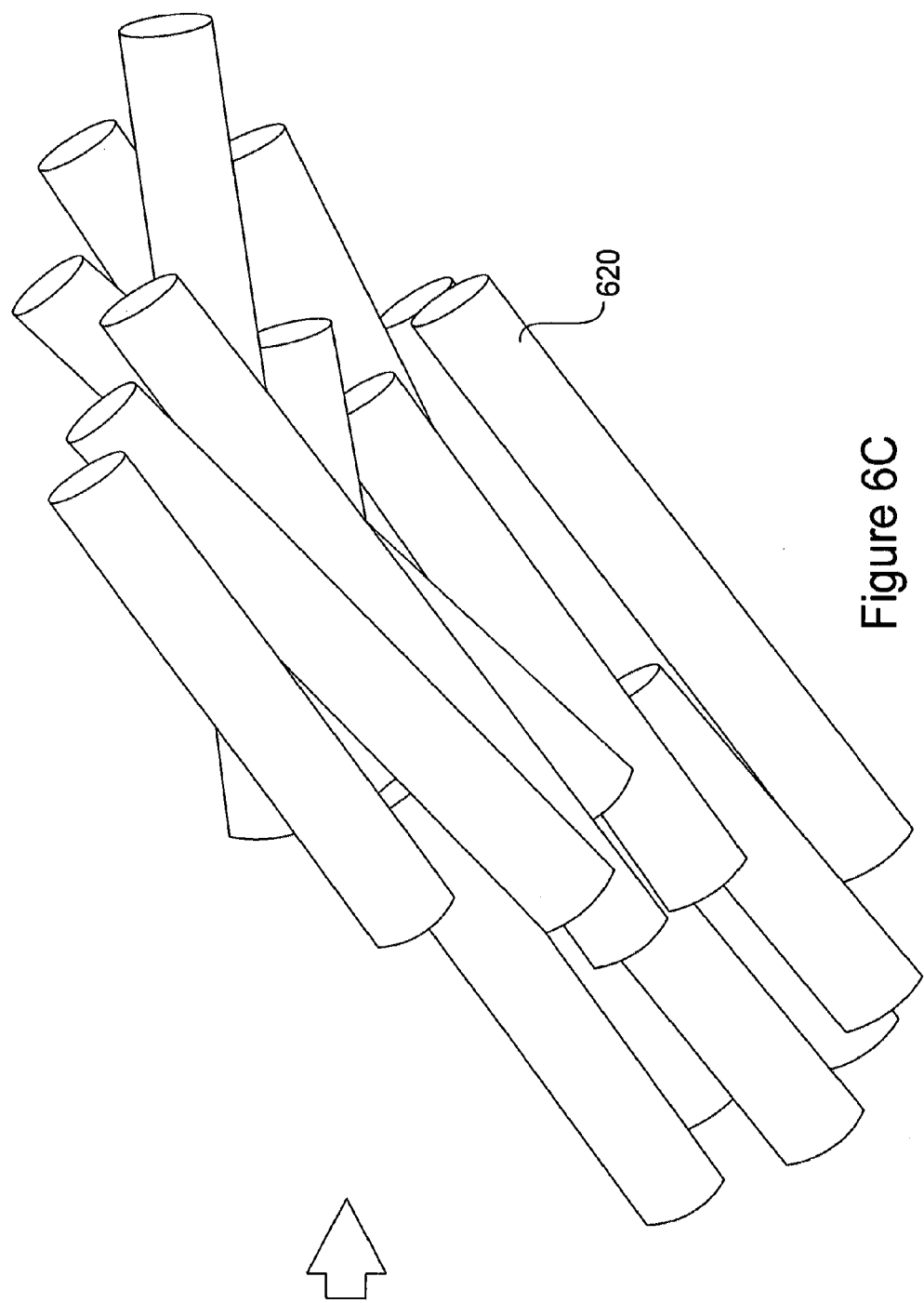

In a next step, shown in FIG. 6C, protofibrils may aggregate together to form fibrils. In FIG. 6C, each cylindrical object, such as cylindrical object 620, represents a protofibril comprising anywhere from five to 100 amyloidogenic intermediate molecules. The aggregation is thought to be somewhat disordered, as shown in FIG. 6C. Although FIG. 6C shows essentially a clump of protofibrils, the protofibrils may be somewhat ordered along at least one dimension and may thus form long fibrils or filaments, much like rope is formed from twisting together short strands of fibrous material.

Figure 6D:
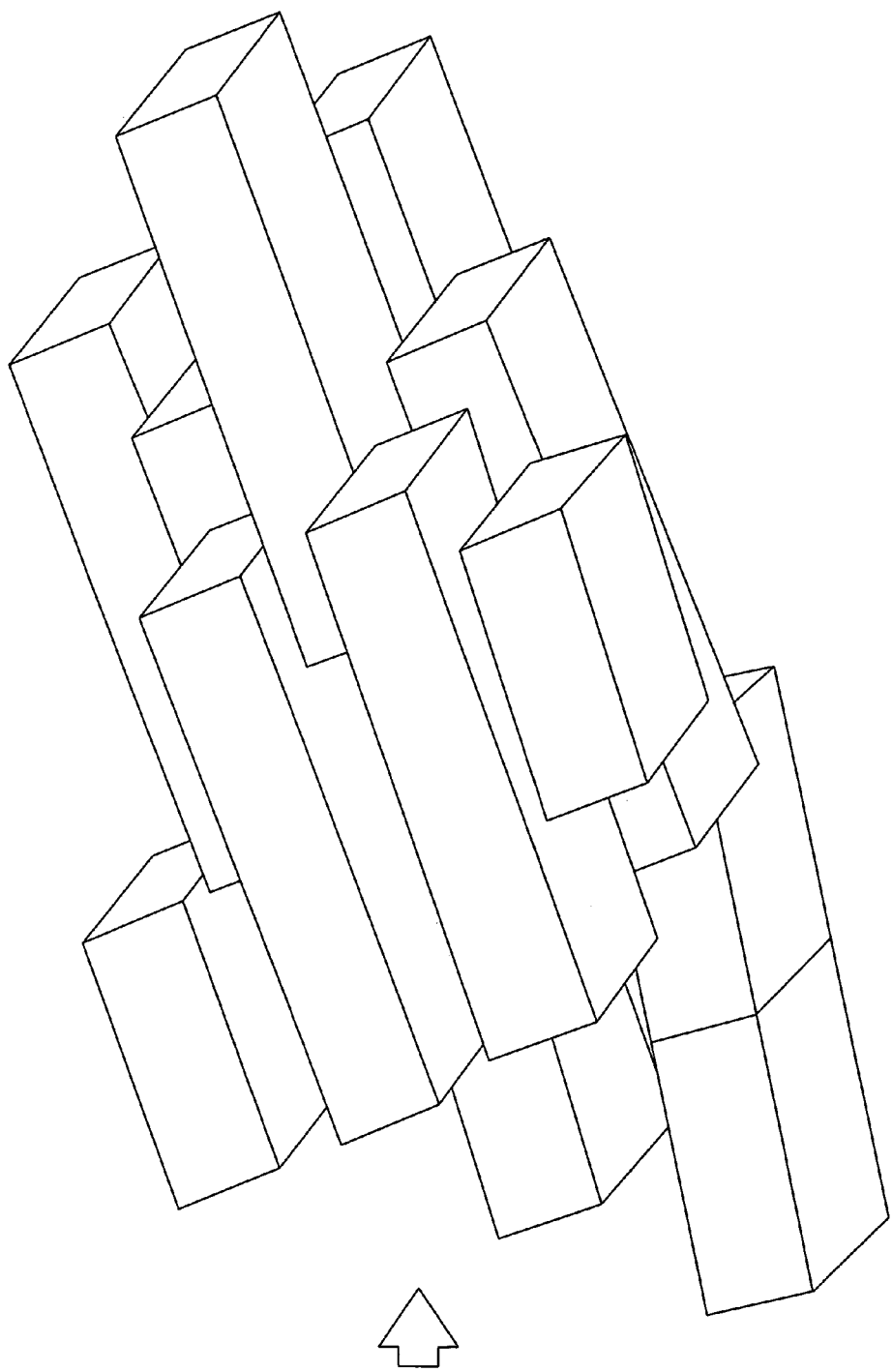

As shown in FIG. 6D, at some point in the process, the amyloid intermediates within protofibrils or fibrils may again change conformationally to a somewhat different structure in which they more closely associate with one another, form stronger associations, more densely pack together, and/or otherwise reach a conformational state that favors long-term stability of higher-order aggregates, such as fibrils, plaques, and other dense, insoluble aggregations. For example, the amount of β-sheet secondary structure may increase in the higher-order aggregates with respect to both the amyloidogenic intermediates and amyloidogenic-precursor proteins and polypeptides. The additional β-sheet structure may include extensive cross-β-sheet structures by which individual proteins are linked together into an insoluble aggregate or matrix.

While the general sequential steps of conformational change and aggregation, illustrated in FIGS. 6A-D, are thought to underlie many amyloid diseases, the specific details have not yet been elucidated. So far, only comparatively low-resolution-structural-information-producing techniques have been applied to characterize the conformations and structures of the amyloidogenic intermediates and higher-order aggregates, the results of which generally comprise repeat-distance constraints and indications of the presence of certain types of secondary-structure motifs and interatomic interactions. Such constraints may be variously interpreted, and are insufficient to propose high-resolution structures.

Lacking the traditional methods for elucidating structure and conformation of the amyloidogenic intermediates and higher-order aggregates, researchers have applied molecular-dynamics computational simulations ("MD") in order to model the conformation and structures of the amyloidogenic intermediates and higher-order aggregates. MD simulations may be performed using the program Encad or the program Ilmm. MD simulations start with a molecule in a conformation for which the energy has been minimized and employ mathematical models of force fields about atoms to iteratively compute shifts or adjustments to the conformation that further minimize overall energy of the conformation. Somewhat surprisingly, the MD simulations have consistently shown that extended-α-strand and α-sheet secondary structure may be present in the amyloidogenic intermediates and protofibrils. As discussed in the next subsection, extended α-strand and α-sheet secondary structure in a first amyloidogenic intermediate provides two unusual docking sites for complementary extended α-strand or α-sheet regions in second and third amyloidogenic intermediates, allowing the amyloidogenic intermediates to form oligomeric structures through strong, non-covalent cross-extended-α-strand and cross-α-sheet secondary-structure bonding.

Currently, the cytotoxic effects produced during the course of amyloid diseases are not well understood. While the presence of higher-order aggregates of amyloidogenic-precursor proteins and amyloidogenic-precursor polypeptides within organisms may disrupt normal cell and organ functions, it is currently thought that the amyloidogenic intermediates and initial, smaller aggregates, such as protofibrils, may be responsible for the bulk of the cytotoxic effects observed in amyloid diseases. At least one antibody has been identified that binds to soluble oligomeric amyloidogenic intermediates, but does not bind insoluble fibrils, and does inhibit toxicity. While many believe that the conformational change that produces amyloidogenic intermediates arises either spontaneously, particularly in low pH environments, or may be induced by essentially infective amyloidogenic intermediates or protofibrils, the cause and course of specific pathologies are still not fully explained. However, generation of amyloidogenic intermediates and higher-order aggregates are certain to play a fundamental role in the various types of pathologies. Therefore, therapeutic agents or physical agents that can interrupt the sequence of conformational changes and aggregation illustrated in FIGS. 6A-D may prove to be valuable therapeutic agents and therapies for treating and preventing amyloid diseases.

Extended α-Strand and α-Sheet Secondary Structure

Figure 7:
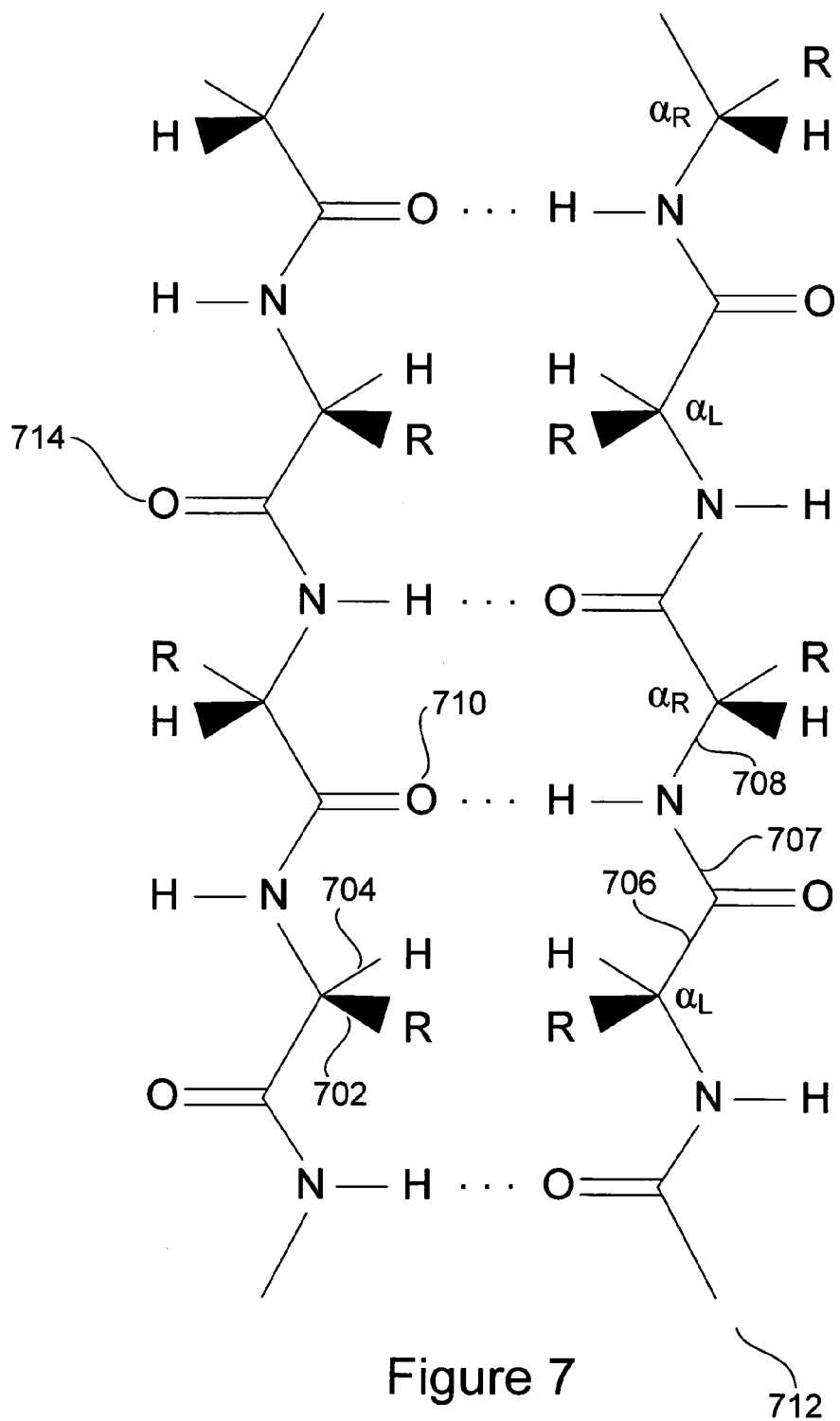
FIG. 7 shows a small two-strand region of β-pleated-sheet secondary structure using conventional organic-chemistry notation.

FIG. 7 shows a small two-strand region of β-pleated-sheet secondary structure using conventional organic-chemistry notation. Note that the conformation of non-polypeptide-backbone substituents about the $C_\alpha$ carbons is indicated by a thickened bond, such as bond 702, for bonds rising up out of the plane of the page and a single-line bond, such as bond 704, for corresponding bonds that fall below the plane of the page. The zigzag-like backbone bonds, such as bonds 706-708 more closely fall within the plane of the page for any particular $C_\alpha$ carbon, although the backbone chains are pleated, in the vertical direction, to form an accordion-like pleated sheet. FIG. 7 can be compared with earlier-discussed FIG. 5, which shows the actual three-dimensional conformation of a small region of β-pleated sheet. As noted in the discussion that refers to FIG. 5, the carbonyl oxygens and amide hydrogens alternate in direction along each strand. Thus, for example, carbonyl oxygen 710 points toward the neighboring strand 712, while carbonyl oxygen 714 points away from the neighboring strand 712. While there is a significant localized dipole moment within the β-pleated-sheet secondary structure approximately orthogonal to the strands, the alternating directions of the carbonyl oxygens and amide hydrogens along the strands produce localized dipole moments with alternating, opposite directions, resulting in a relatively small, cumulative dipole moment for the β-pleated-sheet secondary structure, as a whole.

FIGS. 8A-D illustrate the α-sheet secondary structure, using the same illustration conventions as used to illustrate the β-pleated-sheet secondary structure in FIG. 7. The α-sheet secondary structure shown in FIG. 8A also comprises two separate strands 802 and 804 which may either be two regions of a single polypeptide folded back on itself or may be extended-α-strand regions of two different polypeptides. Note that, unlike in the β-pleated-sheet structure, all of the carbonyl oxygens in the α-sheet structure are oriented in a similar direction. Thus, there is a very large, overall dipole moment for the entire α-sheet secondary structure. Moreover, note that there may be a hydrogen bond between each amino-acid monomer of each strand in the α-sheet secondary structure, as opposed to the β-pleated-sheet secondary structure, which includes fewer inter-strand hydrogen bonds.

Figure 8A:
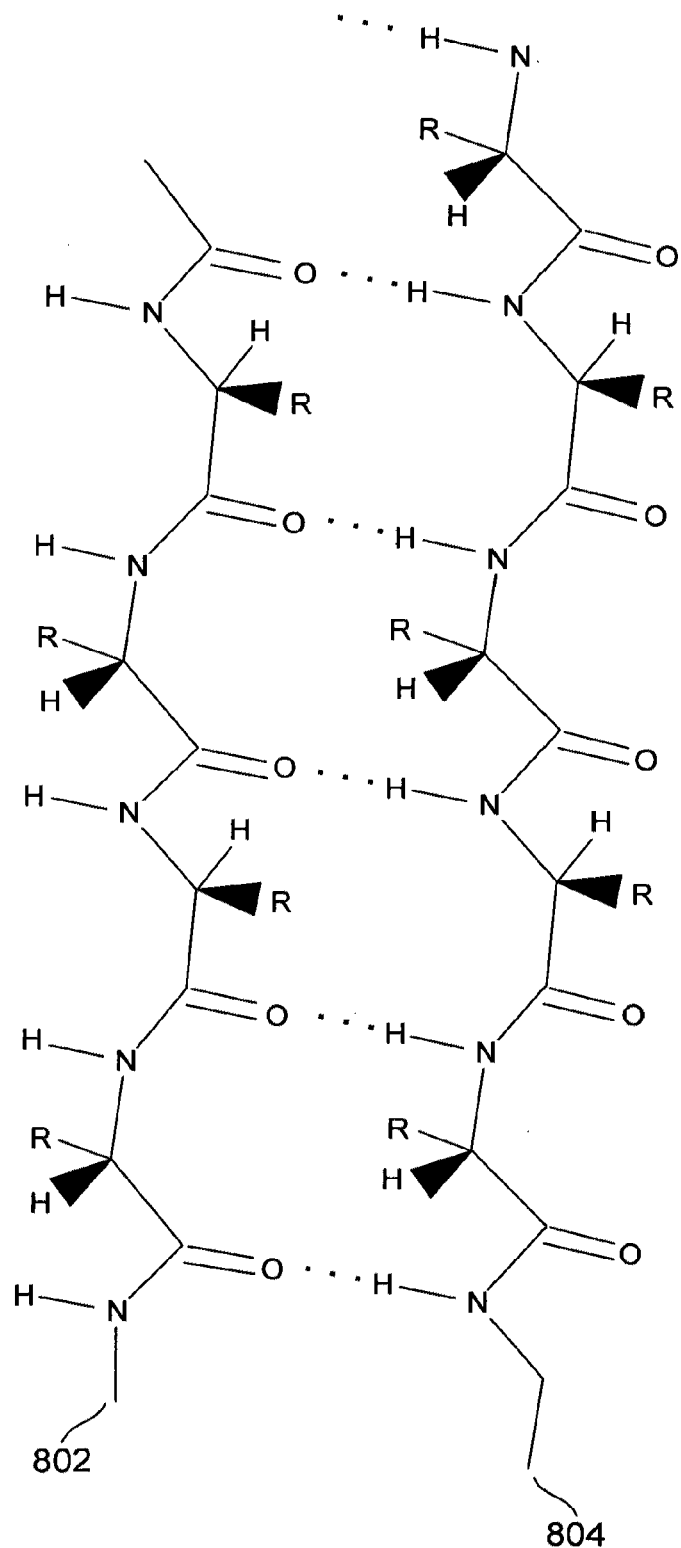
FIGS. 8A-D illustrate the α-sheet secondary structure, using the same illustration conventions as used to illustrate the β-pleated-sheet secondary structure in FIG. 7.
Figure 8B:
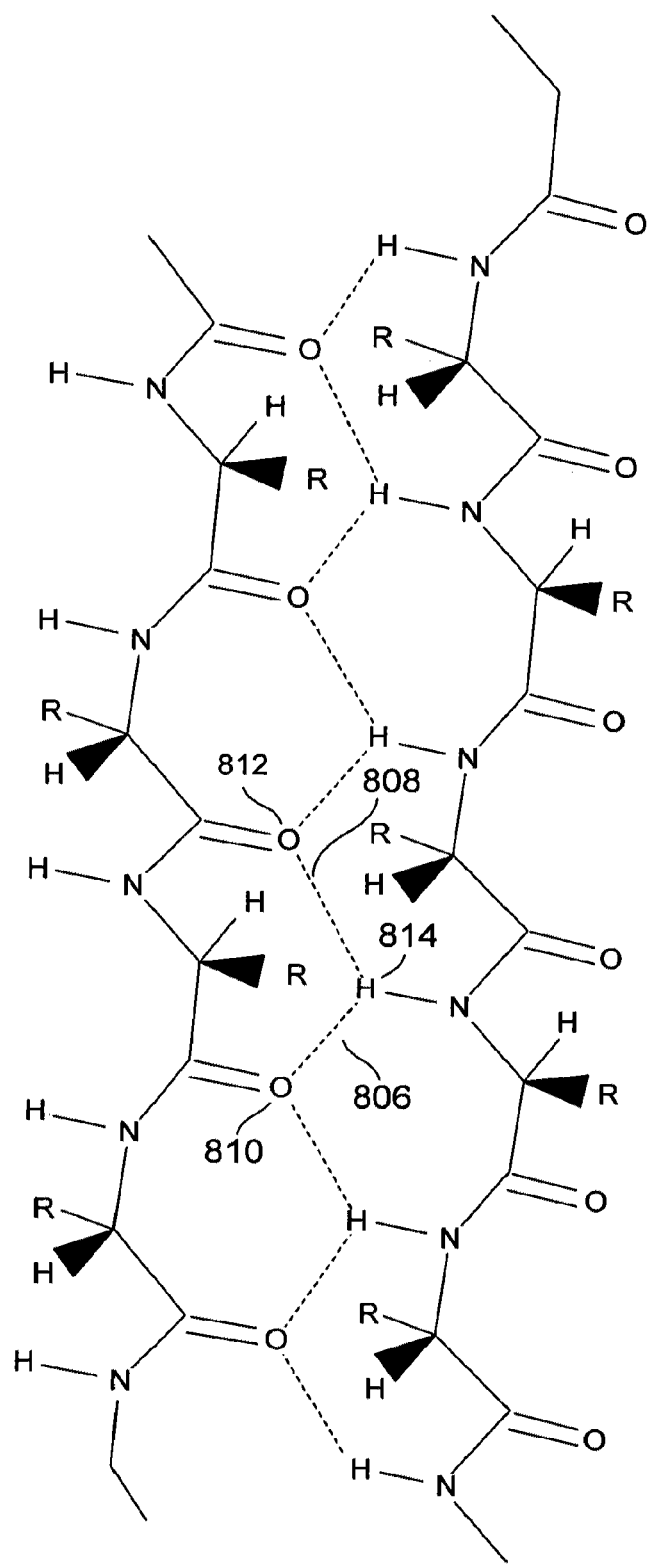
Figure 8C:
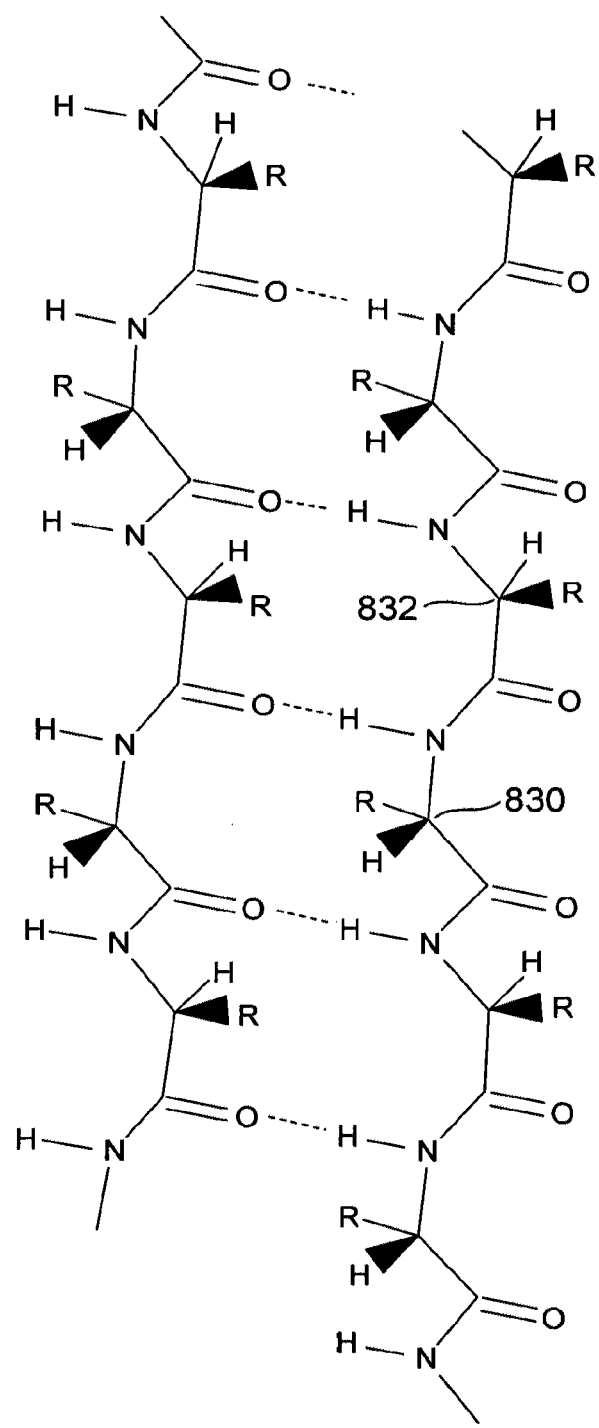

FIG. 8B shows the α-sheet secondary structure shown in FIG. 8A following translation of one strand with respect to the other strand by approximately one-half the length of an amino-acid monomer in a vertical direction. Note that, in this staggered conformation, the inter-strand hydrogen bonding is bifurcated, with hydrogen bonds formed from two adjacent carbonyl oxygens to each amide hydrogen, such as hydrogen bonds 806 and 808 between carbonyl oxygens 810 and 812 and amide hydrogen 814. Note also that the slight translation of the two strands with respect to one another involves only a weakening of the hydrogen bonds shown in FIG. 8A and formation of additional hydrogen bonds, as shown in FIG. 8B. Thus, translation of extended α-strand polypeptides with respect to one another may have a relatively low thermodynamic barrier. FIG. 8C shows the two strands shown in FIG. 8A and FIG. 8B with an additional translation with respect to one another in the vertical direction by one-half the length of an amino-acid residue. As can be observed by comparing FIG. 8A to FIG. 8C, translation of one strand with respect to another by a full amino-acid residue length produces an equivalent structure.

Figure 8D:
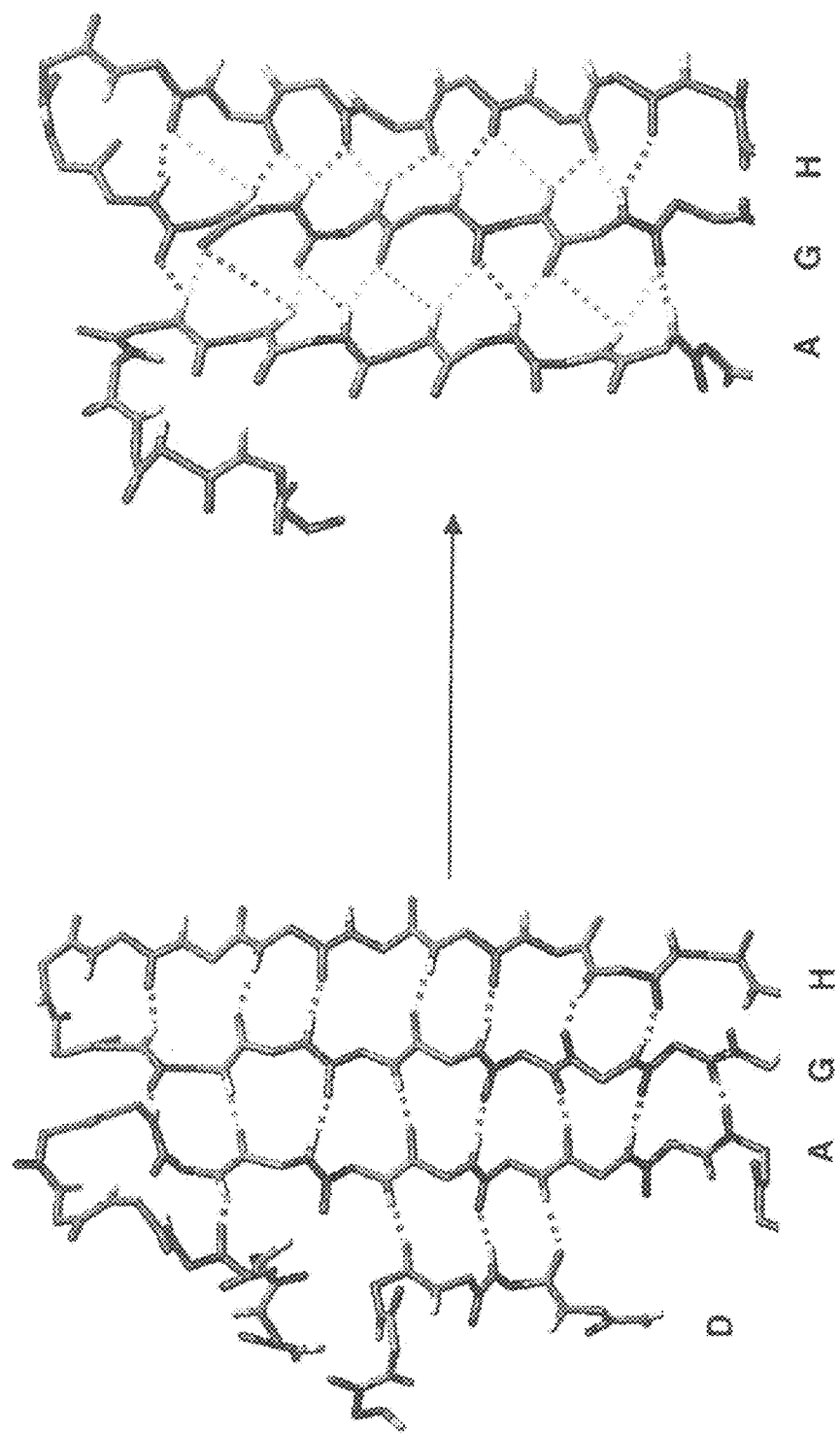

FIG. 8D shows that P-pleated-sheet secondary structure can reversibly change to α-sheet secondary structure. The β-pleated-sheet-to-α-sheet transformation and α-sheet-to-β-pleated-sheet transformation may occur by consecutive, low-thermodynamic-barrier, sequential Φ/Ψ angle rotations that sequentially flip conformations about the $C_\alpha$ atoms. Such transformations may underlie transformation of amyloidogenic-precursor-protein conformation to amyloidogenic-intermediate conformation transformations as well as subsequent amyloidogenic-intermediate conformation to higher-order aggregate-monomer conformation transformations.

Another feature of extended α-strand and α-sheet secondary structure is that the conformation about each successive $C_\alpha$ carbon along each extended α-strand backbone alternates between that typical of a right-handed α helix, or $\alpha_R$, and the conformation typically of a left-handed α helix, $\alpha_L$. In other words, referring to FIG. 8C, were $C_\alpha$ carbon 830 to have the $\alpha_L$ conformation, or, in other words, Φ/Ψ angles typical of $C_\alpha$ Φ/Ψ angles in a left-handed α helix, the next $C_\alpha$ carbon 832 would have a conformation typical of a $C_\alpha$ carbon in a right-handed αhelix, $\alpha_R$. Thus, $\alpha_L$ and $\alpha_R$ domains alternate with each successive $C_\alpha$ carbon along the polypeptide backbone of extended α-strand and α-sheet polypeptides.

Figure 9:
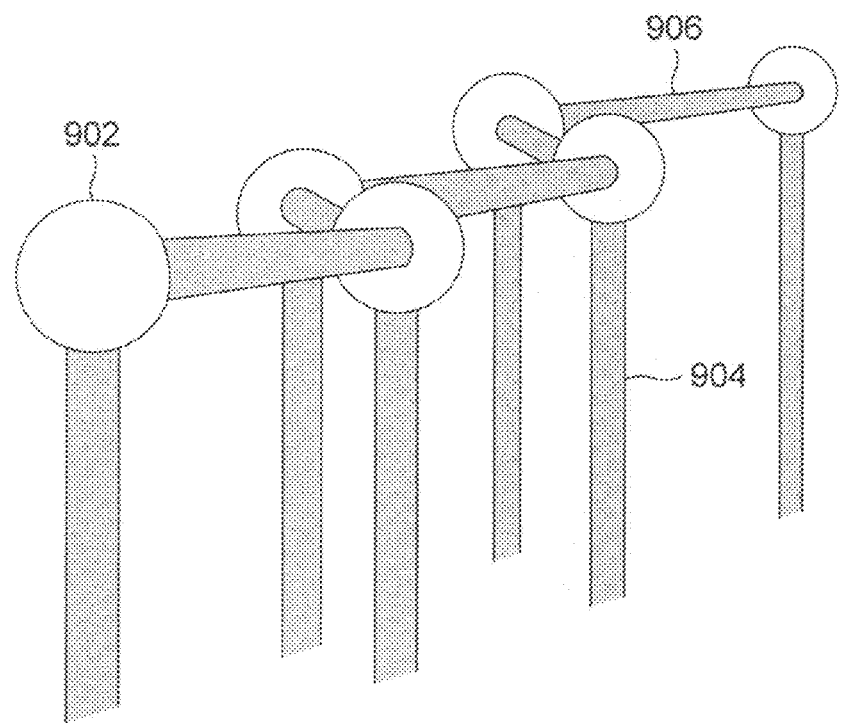
FIG. 9 illustrates the zigzag-like pattern of carbonyl oxygens and amide hydrogens observed along the edges of extended α-strand or α-sheet secondary structure.
Figure 10:
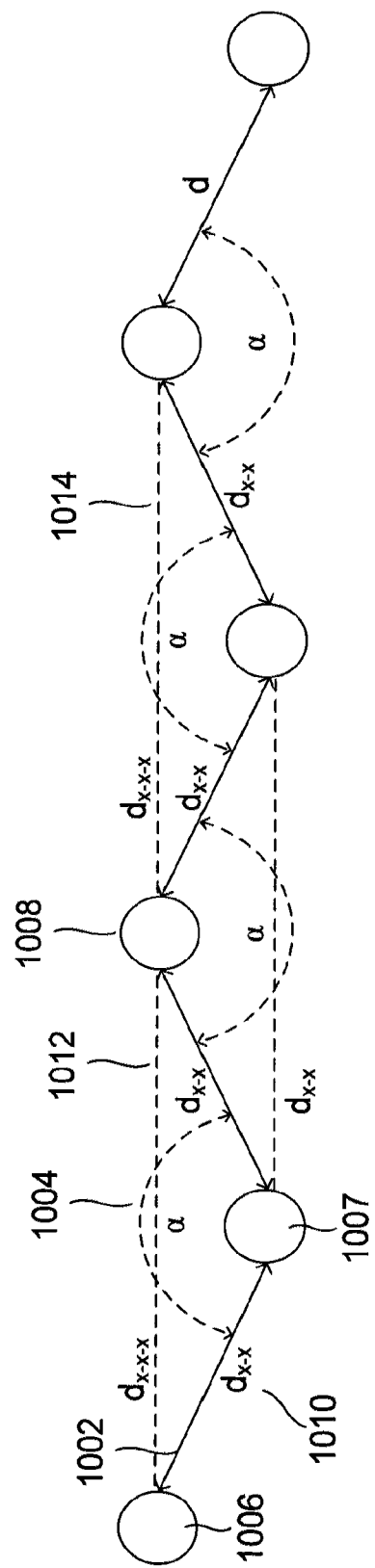
FIG. 10 shows the same carbonyl oxygens or amide hydrogens at the edge of an extended-α-strand region looking down on the carbonyl oxygens or amide hydrogens in the direction of the vertical bonds, such as vertical bond 904, in FIG. 9.
Figure 11A:
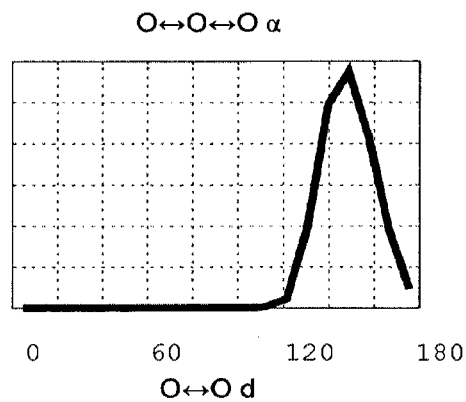
FIGS. 11A-E plot the angles α and distances $d_{X-X}$ for the zigzag-like arrangement of carbonyl oxygens, amide hydrogens, and the carbonyl carbons as discussed with reference to FIGS. 9-10.
Figure 11B:
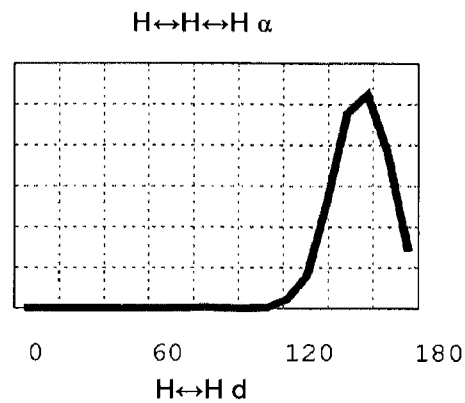
Figure 11C:
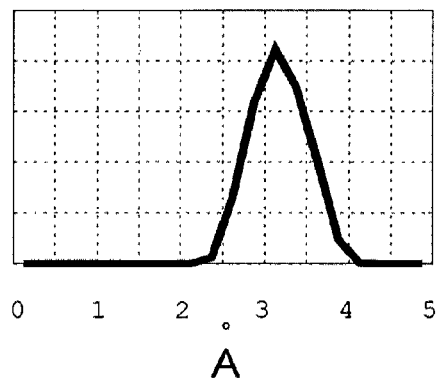
Figure 11D:
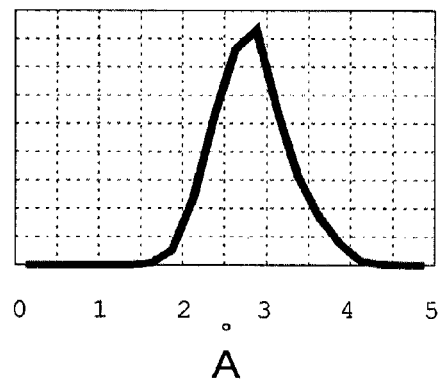
Figure 11E:
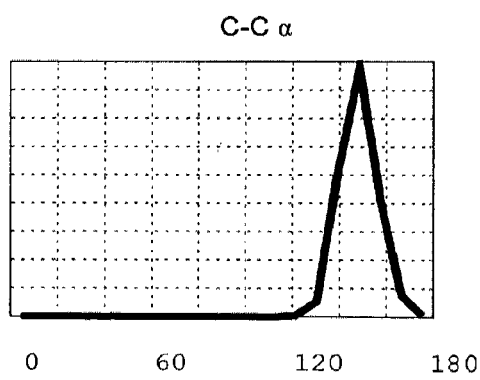

FIG. 9 illustrates the zigzag-like pattern of carbonyl oxygens and amide hydrogens observed along the edges of extended α-strand or α-sheet secondary structure. In FIG. 9, each atom, such as atom 902, represents either exposed carbonyl oxygens at the carbonyl-oxygen-rich edge of an extended α-strand region or exposed amide nitrogens at the opposite, amide-hydrogen-rich edge of the extended α-strand region. The carbonyl oxygens and amide hydrogens are involved in the inter-strand hydrogen bonds illustrated in FIGS. 8A-C. The vertical bonds, such as bond 904, represent either N—H bonds or C=O bonds. The roughly horizontal, zigzag elements, such as element 906, represent the distances between adjacent carbonyl oxygens, $d_{O-O}$, or adjacent amide hydrogen atoms $d_{H-H}$, rather than chemical bonds. FIG. 10 shows the same carbonyl oxygens or amide hydrogens at the edge of an extended α-strand region looking down on the carbonyl oxygens or amide hydrogens in the direction of the vertical bonds, such as vertical bond 904 in FIG. 9. In FIG. 10, the double-headed arrows, such as double-headed arrow 1002, represent the inter-carbonyl oxygen or inter-amide hydrogen distances $d_{X-X}$, such as distance 906 in FIG. 9. The carbonyl oxygens and amide hydrogens form zigzag-like arrangements, as shown in FIGS. 9 and 10, characterized by the angle α 1004 between three consecutive carbonyl oxygens or amide hydrogens 1006-1008 and an average distance $d_{X-X}$ 1010. The distance between a first and third carbonyl oxygen or amide hydrogen along the zigzag-like arrangement is characterized by a distance $d_{X-X-X}$, indicated by dashed lines 1012 and 1014. The carbonyl carbons of the polypeptide backbone also form a corresponding, zigzag structure characterized by distances $d_{C-C}$ and $d_{C-C-C}$ and an angle α between each successive triplet of carbonyl carbons.

FIGS. 11A-E plot the angles α and distances $d_{X-X}$ for the zigzag-like arrangement of carbonyl oxygens, amide hydrogens, and the carbonyl carbons as discussed with reference to FIGS. 9-10. These angles and distances are computed from a large number of MD simulations and protein structures obtained by NMR and x-ray crystallography methods that are contained in various databases, such as the Protein Data Bank ("PDB"). As can be seen in FIGS. 11A-E, the carbonyl-carbon angles α cluster relatively narrowly around 148°±26°. The carbonyl-oxygen distances $d_{O-O}$ cluster relatively narrowly around 3.1±0.4 Å, with $d_{O-O-O}$ of 5.95±0.8 Å. The amide-hydrogen angles α cluster relatively narrowly around 159°±30°. The amide-hydrogen distances $d_{H-H}$ cluster relatively narrowly around 2.9±0.8 Å, with $d_{H-H-H}$ of 5.6±1.6 Å. The carbonyl-carbon angles α cluster relatively narrowly around 147.6°±9.0°.

Figure 12A:
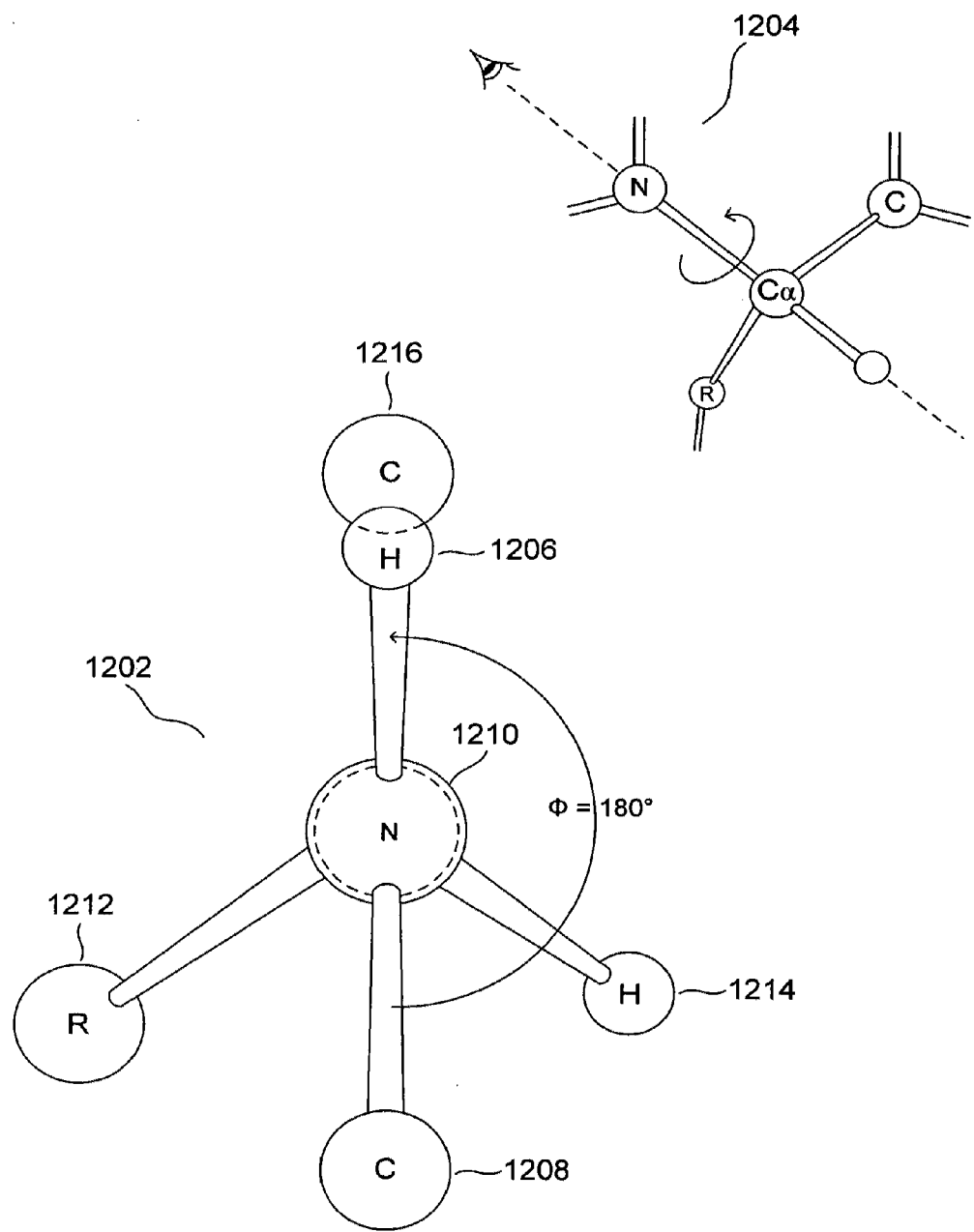
FIGS. 12A-C illustrate the conformation about the $C_\alpha$—N polypeptide-backbone bond.
Figure 12B:
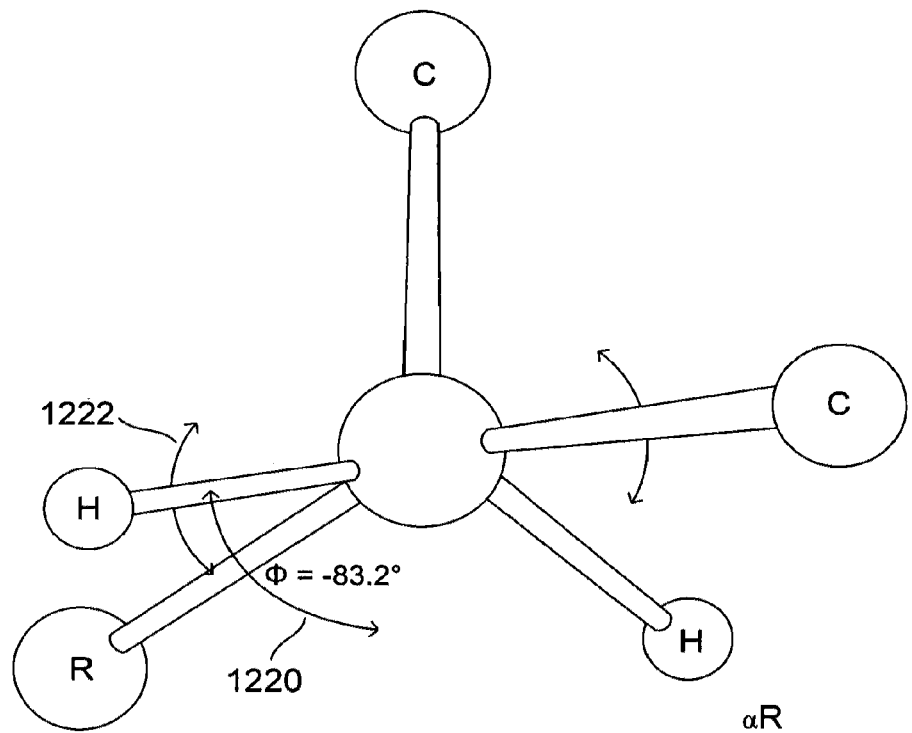
Figure 12C:
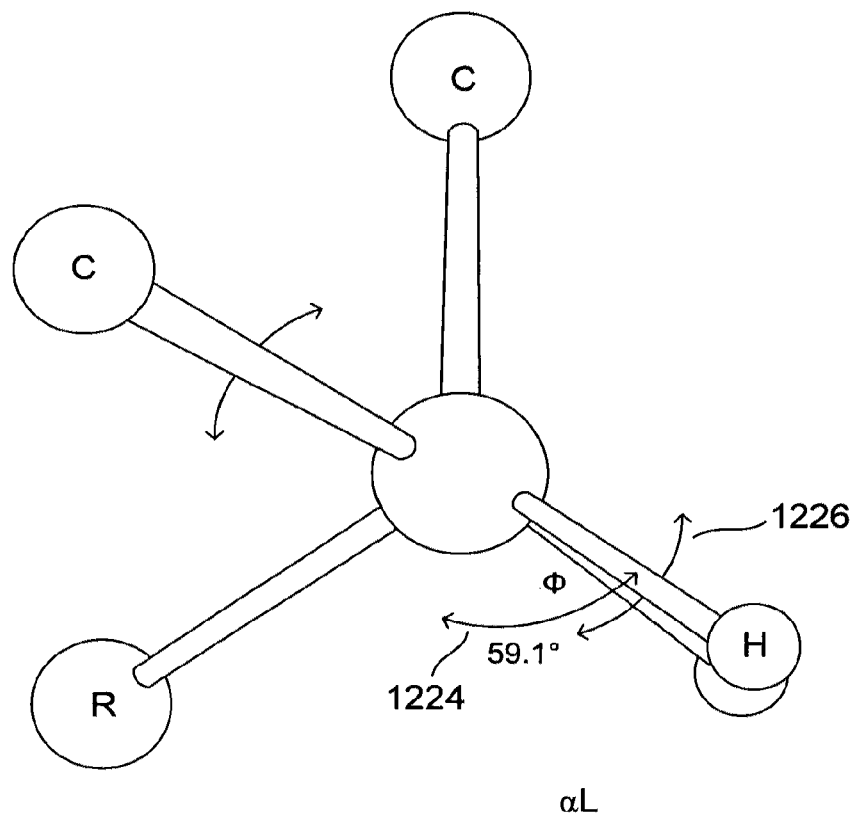
Figure 13A:
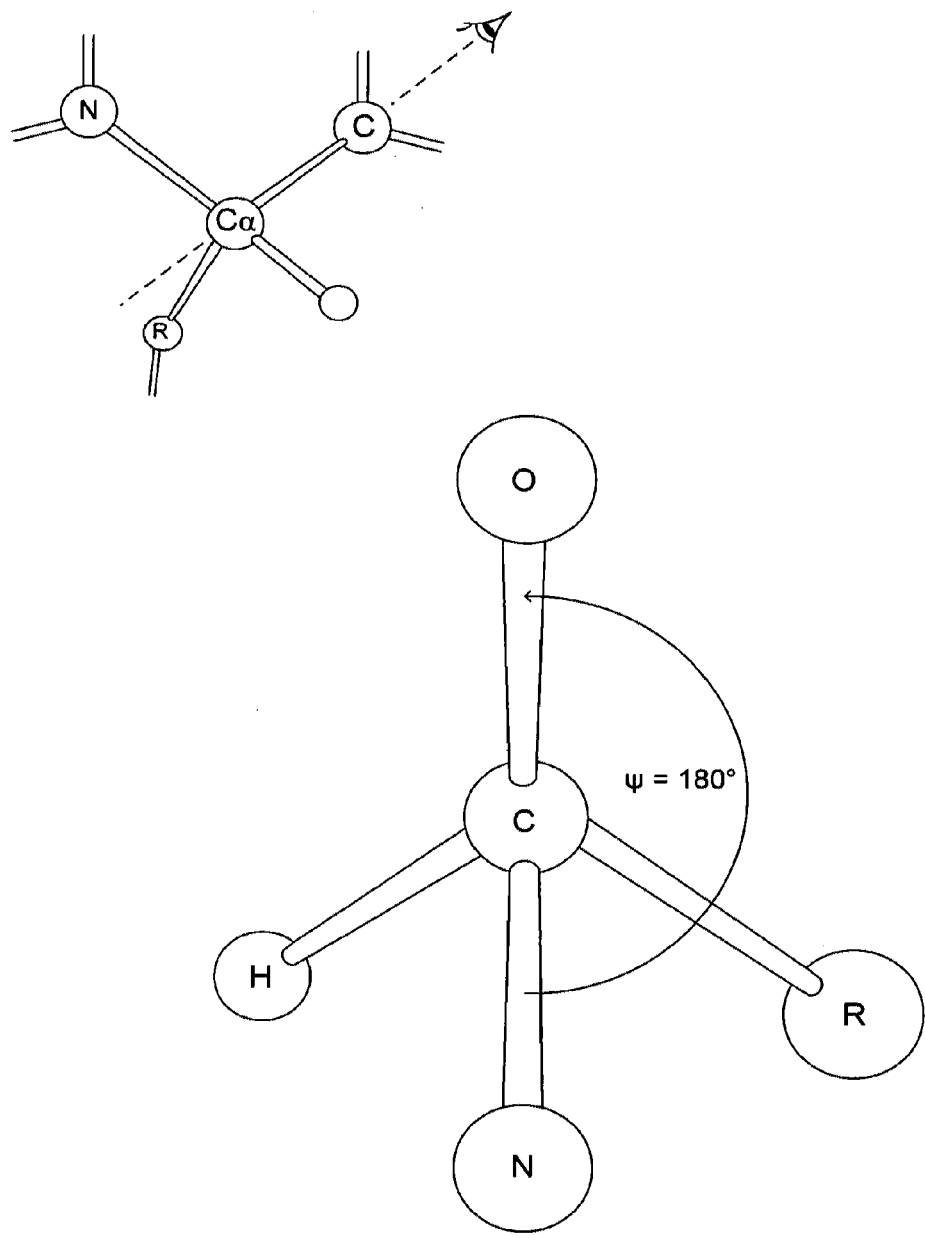
FIGS. 13A-C illustrate the conformation about the $C_\alpha$—C polypeptide-backbone bond.
Figure 13B:
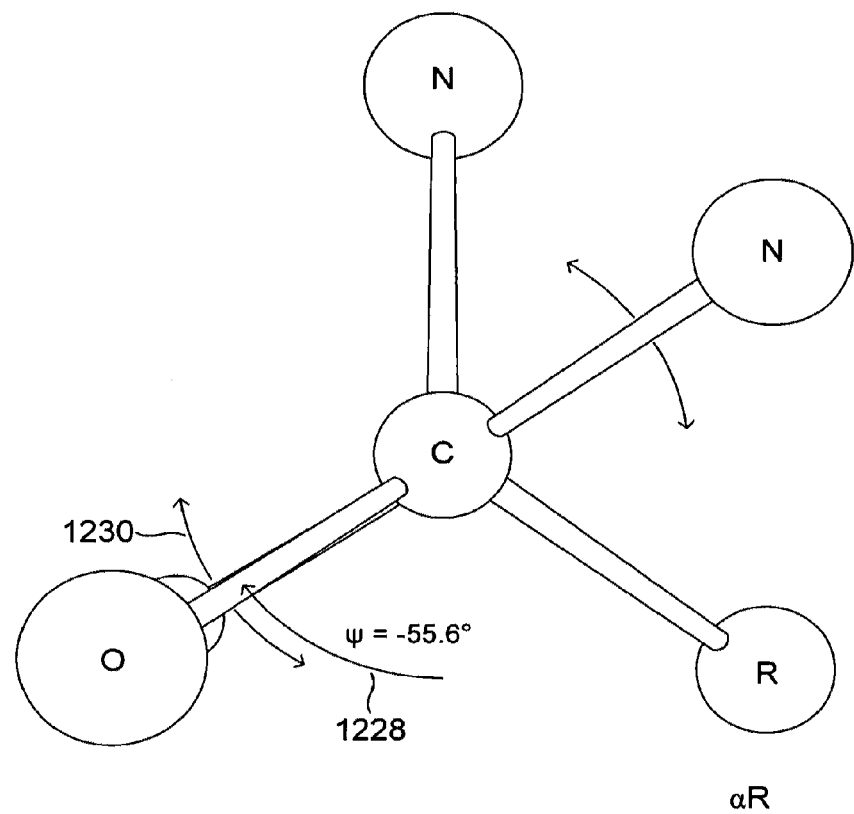
Figure 13C:
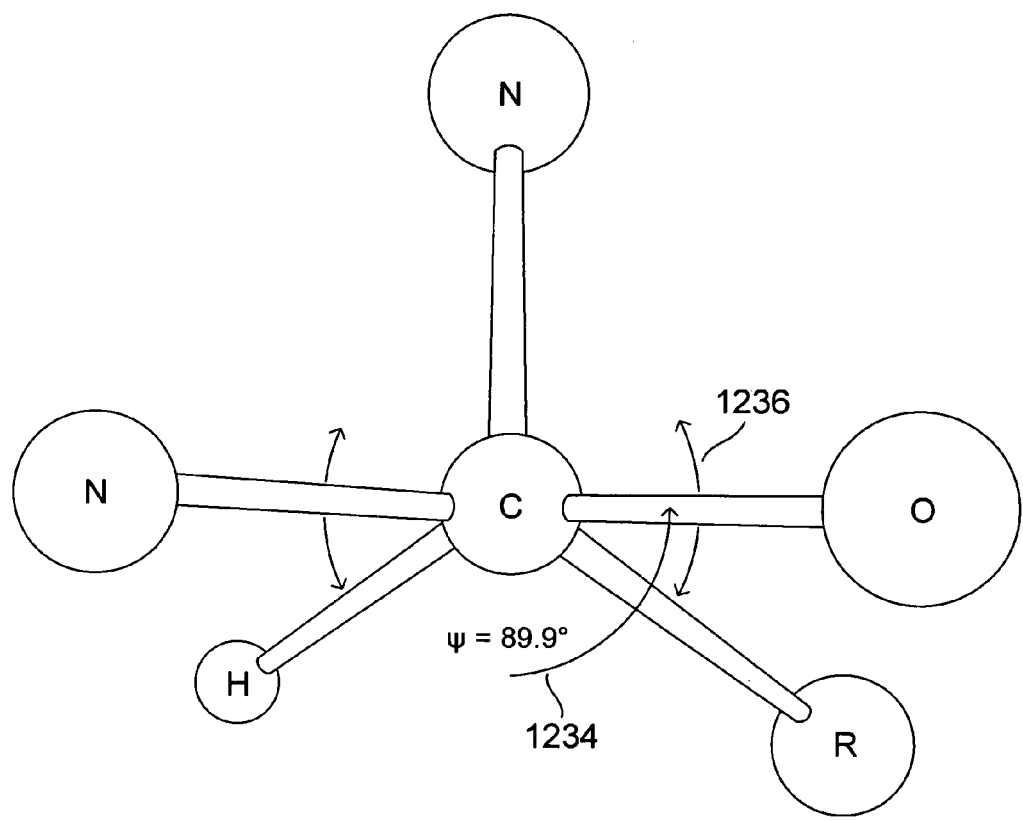
Figures 14A, 14B:
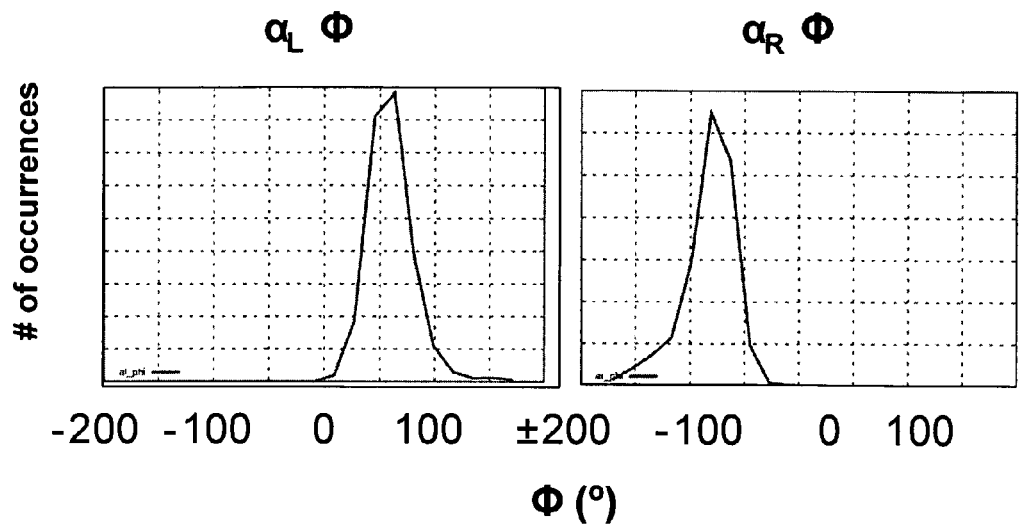
FIGS. 14A-D show graphs of the observed Φ and Ψ angles for $α_L$ and αR domains for a variety of extended-α-strand and α-sheet secondary structure observed in various MD simulations as well as in NMR-determined and X-ray-crystallography-determined three-dimensional protein and polypeptide structures.
Figures 14C, 14D:
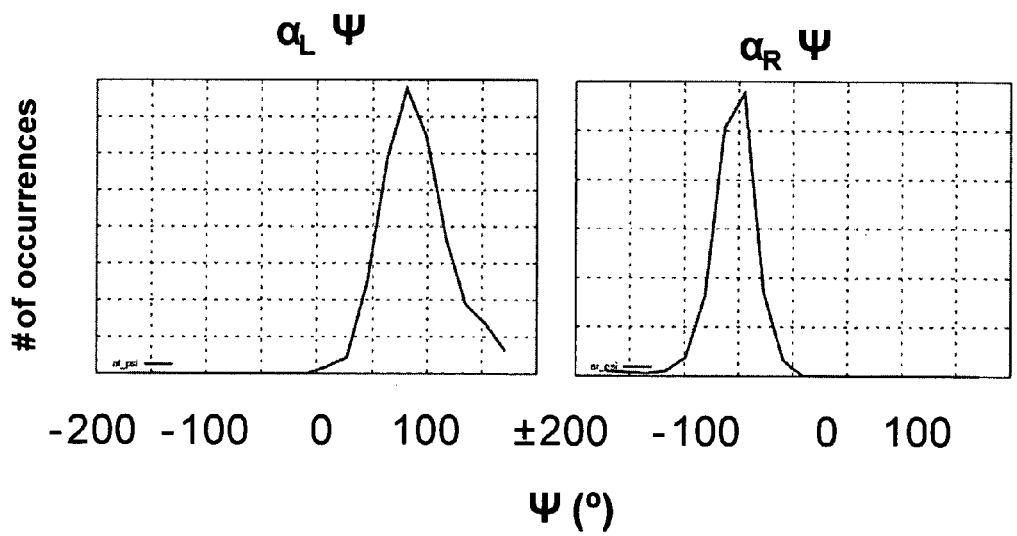

FIGS. 12A-C illustrate the ranges of Φ angles normally observed in extended α-strand and α-sheet secondary structure. FIGS. 12A-C illustrate the conformation about the $C_\alpha$—N polypeptide-backbone bond. In FIG. 12A, the conformation about the $C_\alpha$—N backbone bond 1202 is illustrated as it appears looking downward, on the nitrogen atom, in the direction of the bond 1204. The amide hydrogen 1206, carbonyl carbon 1208, and nitrogen atom 1210 are planar to the nitrogen atom, and extend upward, away from the plane of the page. The first atom of the R group 1212, the hydrogen atom 1214, and the carbonyl carbon atom 1216 attached to the $C_\alpha$ atom, obscured by nitrogen atom 1210, extend downward, below the plane of the page. The N—$C_\alpha$ bond passes through the plane of the page normal to the plane of the page. In FIG. 12A, the torsion angle about the N—$C_\alpha$ bond, or Φ angle, is positioned at 180°. As shown in FIG. 12B, in $\alpha_R$ domains of the extended α-strand secondary structure, the Φ angle 1220 is −83.2°, on average, and varies about the average Φ angle by 48° 1222. As shown in FIG. 12C, for $\alpha_L$ domains of an extended α-strand secondary structure, the Φ angle is, on average, 59.1° 1224 and varies about this average angle by 41.4° 1226. FIGS. 13A-C illustrate the conformation about the $C_\alpha$—C polypeptide-backbone bond. FIGS. 13A-13C illustrate the Ψ angle observed in extended α-strand and α-sheet secondary structure, using the same illustration conventions as used in FIGS. 12A-C to depict the Φ angles. FIG. 13A shows the Ψ angle positioned at 180°. FIG. 13B shows that the average Ψ angle of the $\alpha_R$ domains of extended α-strand polypeptides is −55.6° 1228 and varies over a range of 43.8° 1230. In $\alpha_L$ domains of extended α-strand secondary structure, the average Ψ angle is 89.9° 1234 and varies over 61.2° 1236.

Figure 15:
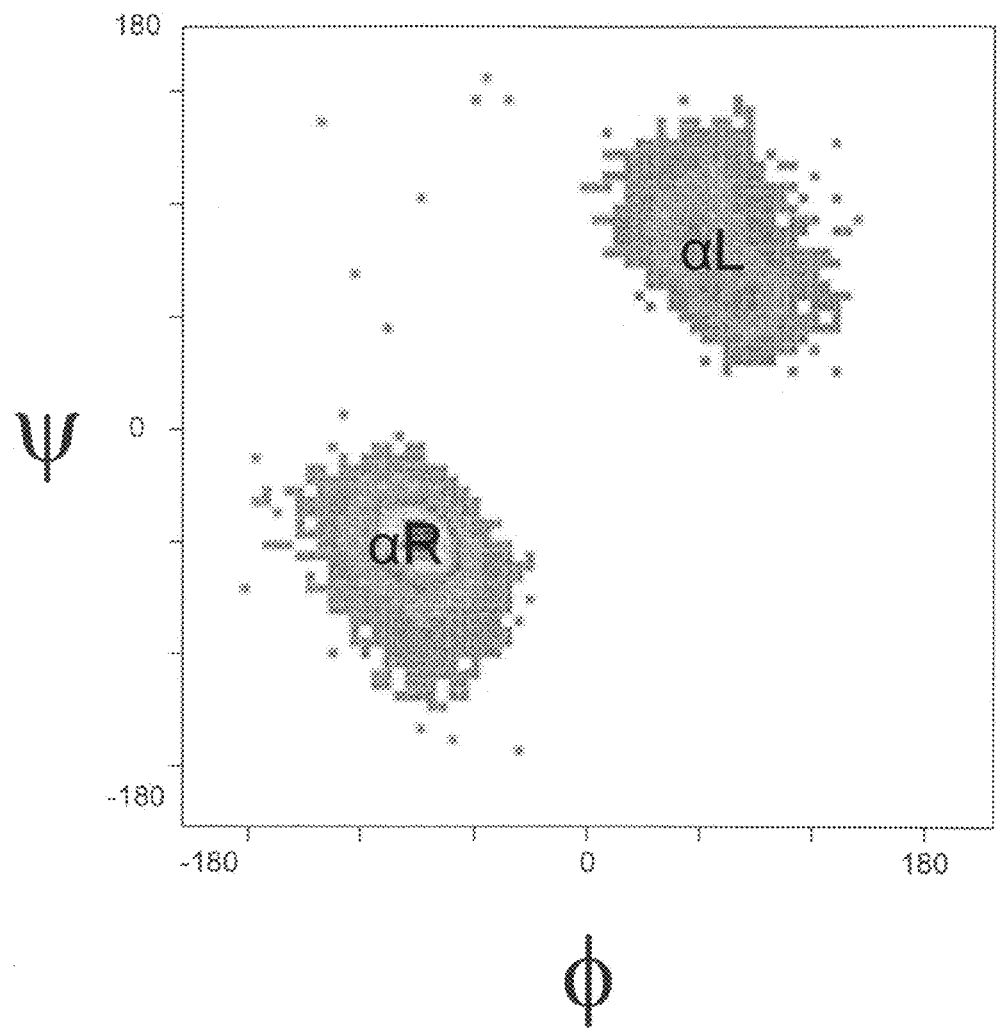
FIG. 15 shows a Ramachandran plot of the Φ/Ψ angle pairs for the $α_R$ and $α_L$ domains of the extended-α-strand and α-sheet domains observed in a variety of simulated structures and in structures determined by NMR and X-ray crystallography.

FIGS. 14A-D show graphs of the observed Φ and Ψ angles for $\alpha_L$ and $\alpha_R$ domains for a variety of extended-α-strand and α-sheet secondary structure observed in various MD simulations as well as in NMR-determined and X-ray-crystallography-determined three-dimensional protein and polypeptide structures. FIG. 15 shows a Ramachandran plot of the Φ/Ψ angle pairs for the $\alpha_R$ and $\alpha_L$ domains of the extended-α-strand and α-sheet domains observed in a variety of simulated structures and in structures determined by NMR and X-ray crystallography.

The zigzag, or pleated, arrangement of carbonyl oxygens that constitutes a first type of binding site in amyloidogenic intermediates, or (−) binding site, and the zigzag, or pleated, arrangement of amide hydrogens that constitutes a second type of binding site in amyloidogenic intermediates, or (+) binding site, complementary to the first type of binding site, or (−) binding site, are, in many ways, ideal targets for amyloidosis inhibitors. These binding sites are uniquely characterized by the above-discussed distance and angle parameters, and the extended-α-strand and α-sheet secondary structure that features these carbonyl-oxygen-rich and amide-hydrogen-rich binding sites are uniquely characterized by the Φ/Ψ torsion angles for alternating $\alpha_L$ and $\alpha_R$ domains of the polypeptide backbone within extended-α-strand and α-sheet secondary structure. As with any such parametric representation of molecular structure, narrower ranges of angles and distances may be used to characterize extended-α-strand and α-sheet secondary structure and the (+) binding site and (−) binding sites featured by extended-α-strand and α-sheet secondary structure. For example, carbonyl-carbon angles α may be alternatively specified as 148°±20°, 148°±15°, or 148°±10°. The carbonyl-oxygen distances $d_{O-O}$ may be alternatively specified as 3.1±0.3 Å, 3.1±0.2 Å, and 3.1±0.1 Å. The amide-hydrogen angles α may be alternatively specified as 159°±30°, 159°±20°, or 159°±10°. The amide-hydrogen distances may be alternatively specified as 2.9±0.6 Å, 2.9±0.4 Å, or 2.9±0.2 Å. The $\alpha_R$ domain Φ/Ψ angles may be alternatively specified as −83.2°±24°/−55.6°±21.9°, −83.2°±15°/−55.6°±15°, or −83.2°±10°/−55.6°±10° and the $\alpha_L$ domain Φ/Ψ angles may be alternatively specified as 59.1°±20.7°/−89.9°±30.6°, 59.1°±15°/89.9°±20°, or −59.1°±10°/89.9°±10°.

The amyloidogenic intermediate prion protein $PrP^{SC}$ is shown, by MD simulations, to feature two exposed extended α-strand polypeptide regions, one with carbonyl oxygens facing out from the bulk of the protein and therefore comprising a (−) binding site, and one with amide hydrogens facing out from the bulk of the protein and therefore comprising a (+) binding site. These two binding sites are complementary, and allow each amyloidogenic intermediate protein to bind, through extended α-strand hydrogen bonding, as illustrated in FIGS. 8A-C, to a complementary extended alpha-strand region of another amyloidogenic intermediate. The amyloidogenic intermediate proteins thus essentially form polymer-like, or beaded-string-like, chains, or protofibrils, held together by hydrogen bonding through extended-α-strand (−) and (+) binding sites. Interestingly, amyloidogenic-intermediate aggregation into protofibrils and higher-order structures may occur at different rates when subjected to magnetic or electric fields. Molecules with dipole moments tend to orient themselves with respect to both electric fields and the magnetic fields, and the extended α-strand and α-sheet secondary structure exhibited by amyloidogenic intermediates exhibit relatively strong dipole moments, as discussed above.

Taken together, the Φ/Ψ angle-pair constraints, carbonyl-oxygen angles, carbonyl-oxygen distances, amide-hydrogen angles, and amide-hydrogen distances, discussed above with reference to FIGS. 9-15, fully characterize the general extended α-strand and α-sheet secondary structure observed in simulated amyloidogenic-intermediate structures and in various protein and polypeptide structures determined by NMR and X-ray crystallography. As can be seen by the narrowness of the graphs of the various angles and distances in FIGS. 11A-E and FIGS. 14A-D, these angles and distances provide relatively tight constraints on the polypeptide conformation. These constraints, in turn, provide very well-defined constraints and parameters for developing therapeutic molecules that may bind to (+) and (−) binding sites exhibited by amyloidogenic intermediates, and thus interrupt the sequence of conformational-transformation and aggregation steps, discussed above with reference to FIGS. 6A-D, that lead to protofibrils, fibrils, and higher-order structures.

Therapeutic Agents for Ameliorating or Preventing Amyloidosis According to Various Embodiments of the Present Invention As discussed in the previous subsection, it appears that amyloidogenic-intermediate aggregation occurs by extensive hydrogen bonding and, perhaps, additional electrostatic and dipole-dipole interactions, between complementary edges of extended-α-strand or α-sheet secondary structure, referred to in this document as (−) and (+) binding sites, respectively, within amyloidogenic intermediates. These carbonyl-oxygen and amide-hydrogen-rich edges are attractive targets for therapeutic agents, for many reasons.

First, extended-α-strand and α-sheet polypeptide secondary structure is rarely observed in non-amyloidogenic proteins and polypeptides. Only 924 structures out of a total of 29,936 structures surveyed in the PDB exhibit extended-α-strand secondary structure, and in the 924 structures, 1,161 occurrences of α-strand are observed. Of the 1,161 occurrences of α-strand, 1093 are three-residue structures, 67 are four-residue structures, and only one has a five-residue stretch. There are no occurrences of α-sheet secondary structure in the surveyed PDB structures. Moreover, in non-amyloidogenic proteins and polypeptides, the observed extended-α-strand secondary structure may not occur as complementary (−) and (+) binding sites extending from the surface of the protein or polypeptide. Therefore, therapeutic agents that specifically target the edges of extended α-strand and α-sheet secondary structure most likely target only amyloidogenic intermediates, and do not inadvertently bind to non-target molecules with concomitant potential side effects.

Second, the carbonyl-oxygen-rich and amide-hydrogen-rich edges of extended α-strand and α-sheet secondary structure provide targets for very strong, specific binding by complementary therapeutic agents and, therefore, when the therapeutic agents can be delivered to sites of amyloidosis within organisms at even relatively small concentrations, there is a strong likelihood that they will strongly or irreversibly bind to the docking sites on amyloidogenic intermediates and inhibit or prevent the chain of events leading from amyloidogenic intermediates to protofibrils, fibrils, and higher-order structure. When the therapeutic agents can be designed to elicit protein-destruction pathways within cells and organisms, or elicit an immune response once bound to the complementary docking sites on amyloidogenic intermediates, the amyloidogenic intermediates complexed with therapeutic molecules may be cleared from cells and organisms, completely halting the chain of events leading to amyloidosis.

Third, judging from the ability of extremely small quantities of exogenous infectious amyloidogenic intermediates to enter animals through the circulatory systems and digestive systems of the organisms and find their way to target locations within the brains of the animals, delivery of chemically similar therapeutic agents to therapeutic targets may be expected to not present a difficult problem. This property of infectious amyloidogenic intermediates may be related to the lack of non-target complementary binding sites in normal cells and organisms as well as an extremely high specificity for particular target amyloidogenic-precursor proteins.

Figure 16A:
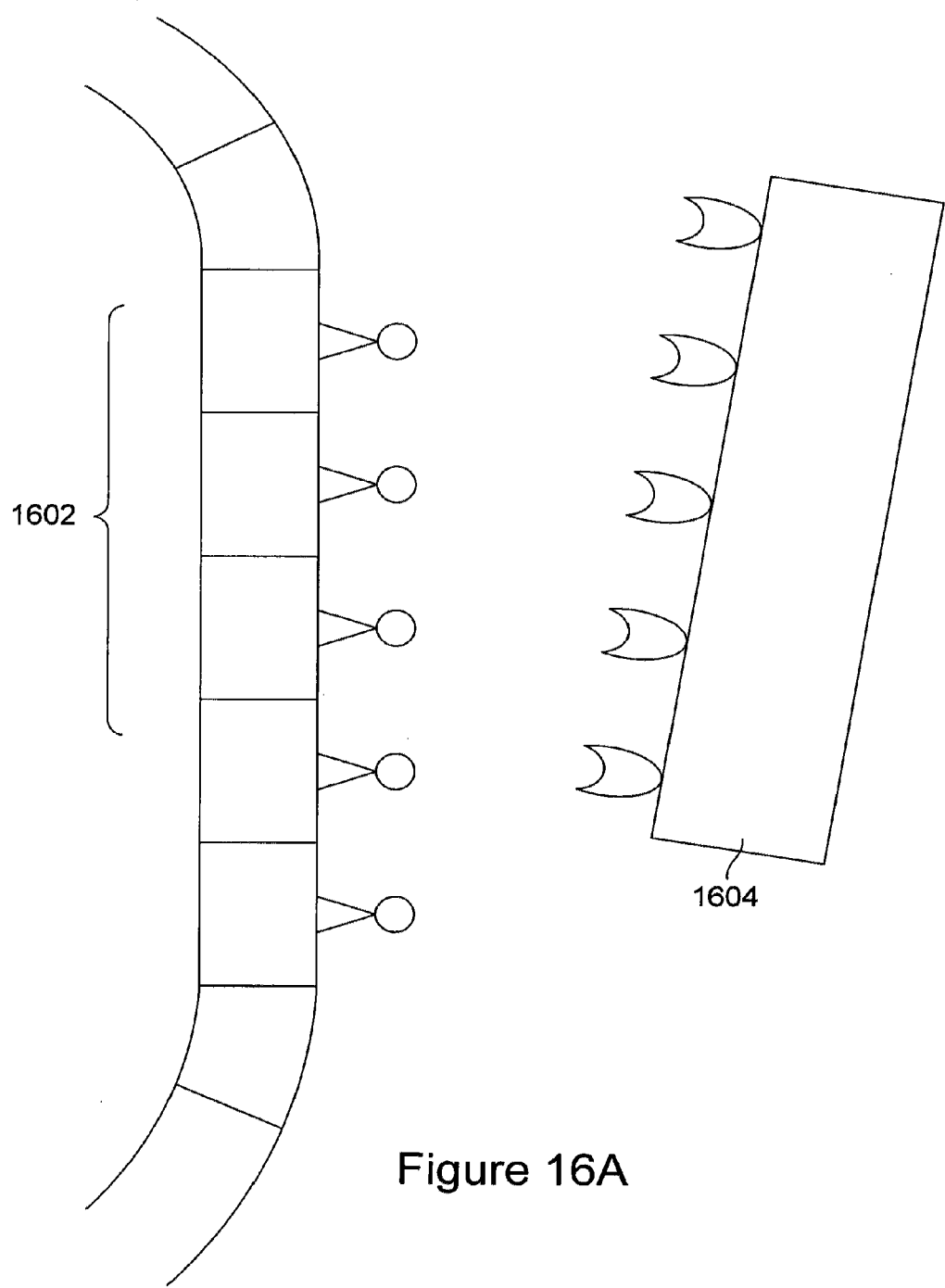
FIGS. 16A-19 provide schematic-like, abstract illustrations of various possible strategies for designing therapeutic agents against extended-α-strand and α-sheet secondary structure exhibited by amyloidogenic intermediates.
Figure 16B:
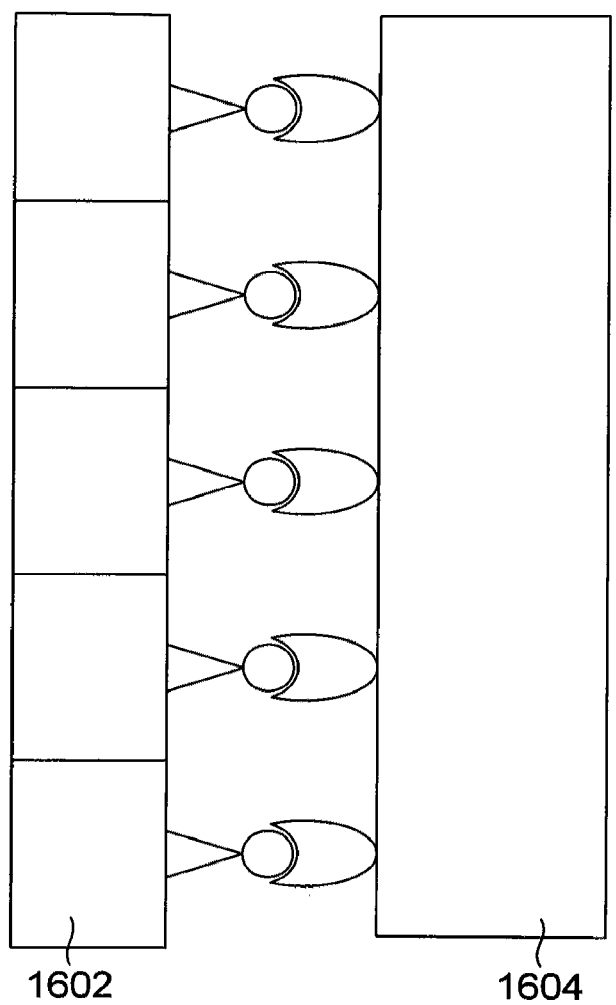

FIGS. 16A-19 provide schematic-like, abstract illustrations of various possible strategies for designing therapeutic agents against extended-α-strand and α-sheet secondary structure exhibited by amyloidogenic intermediates. FIG. 16A shows a local extended α-strand region 1602 of an amyloidogenic intermediate and a complementary therapeutic agent 1604 in solution. As shown in FIG. 16B, when properly designed, the therapeutic agent may tightly bind to either the zigzag-like arrangement of carbonyl oxygens, or (−) binding site, or to the zigzag-like arrangement of amide hydrogens, or (+) binding site, along an edge of the extended α-strand or α-sheet secondary structure. Tight binding, alone, by properly designed therapeutic agents, as shown in FIG. 16B, may scavenge any amyloidogenic intermediates that spontaneously arise, by conformational transformation, or that are conformationally recruited by the presence of protofibrils or amyloidogenic intermediates of exogenous origin, and may thus completely inhibit amyloidosis. As discussed above, the therapeutic agent 1604 may additionally, once bound to the complementary extended α-strand or α-sheet secondary structure of the amyloidogenic intermediate 1602, additionally elicit removal and destruction of the complex by normal protein-degradation systems within cells and organisms or may elicit an immune response leading to degradation and clearance of the complex from cells and organisms.

Figure 17:
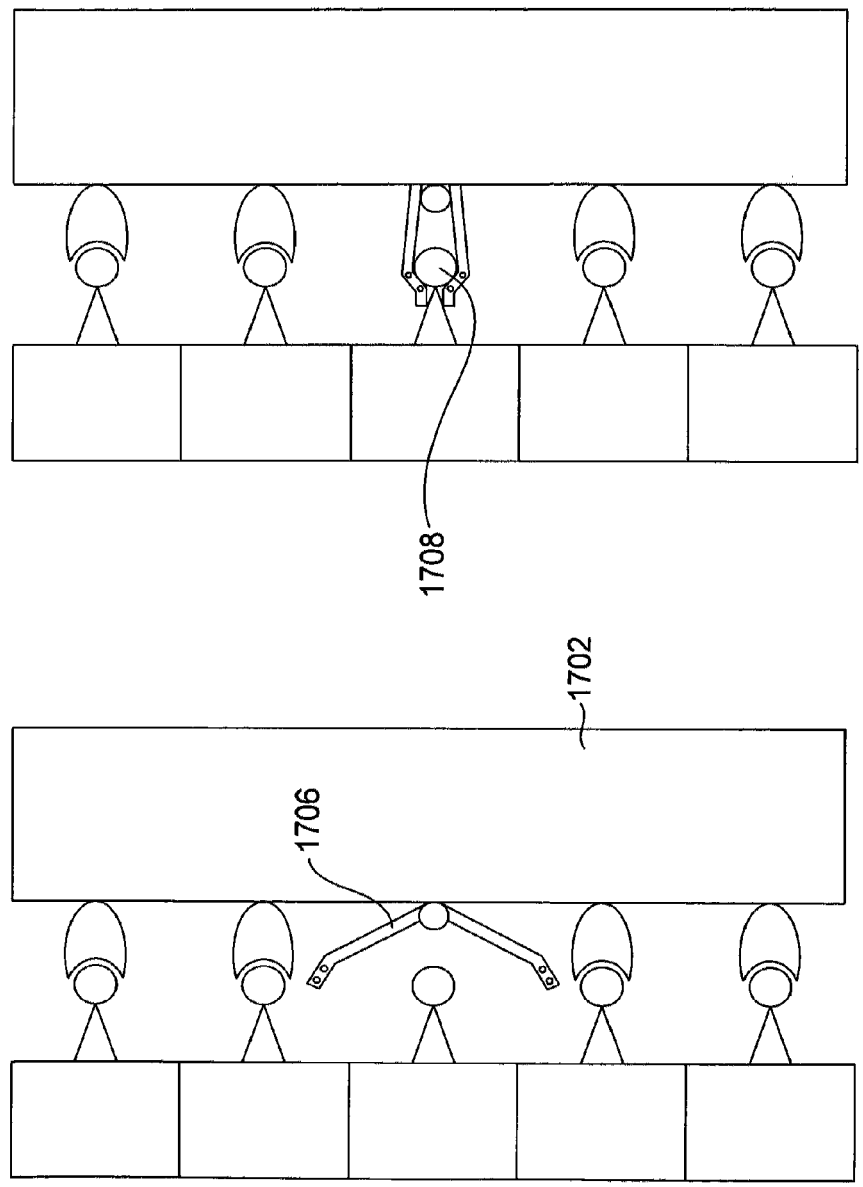

FIG. 17 illustrates an alternative strategy for designing therapeutic agents against extended-α-strand and α-sheet secondary structure exhibited by amyloidogenic intermediates. As shown in FIG. 17, a therapeutic agent 1702 may be designed to covalently bind to the extended α-strand or α-sheet edge of an amyloidogenic intermediate once the therapeutic agent binds to the (−) or (+) binding site via hydrogen bonding or electrostatic interaction. In FIG. 17, the pincer-like element 1706 is shown to close around a carbonyl oxygen or amide hydrogen 1708, representing covalent binding by a chemical substituent of the therapeutic agent to the carbonyl oxygen or amide hydrogen, or perhaps covalent bonding to the amide nitrogen, carbonyl carbon, or even side chains of the amino-acid monomer containing the carbonyl oxygen. While hydrogen bonding or electrostatic interactions may be sufficient for therapeutic purposes, the addition of a reactive substituent that covalently binds to the extended α-strand region of an amyloidogenic intermediate may even more effectively disable the extended α-strand binding or docking site.

Figure 18:
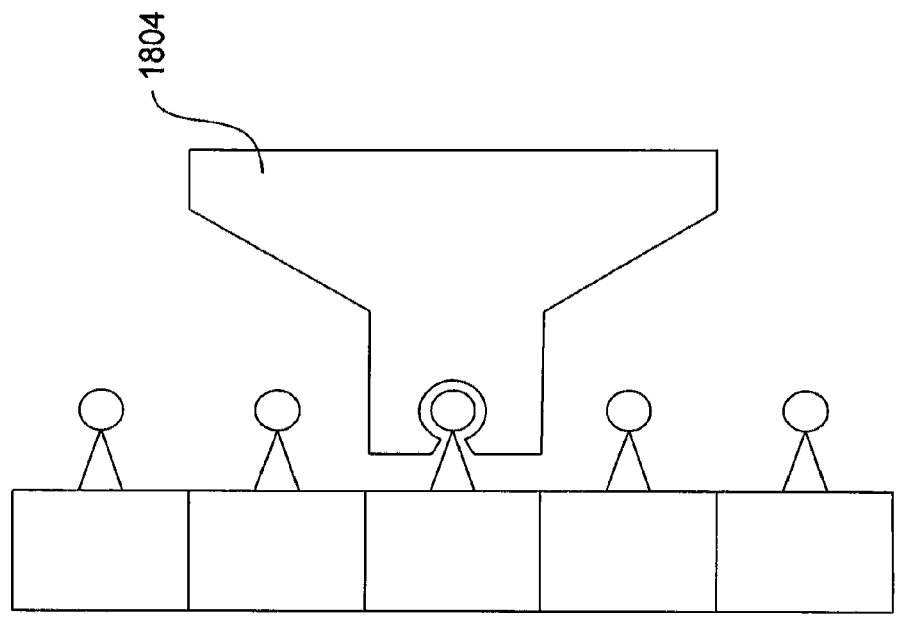
Figure 18:
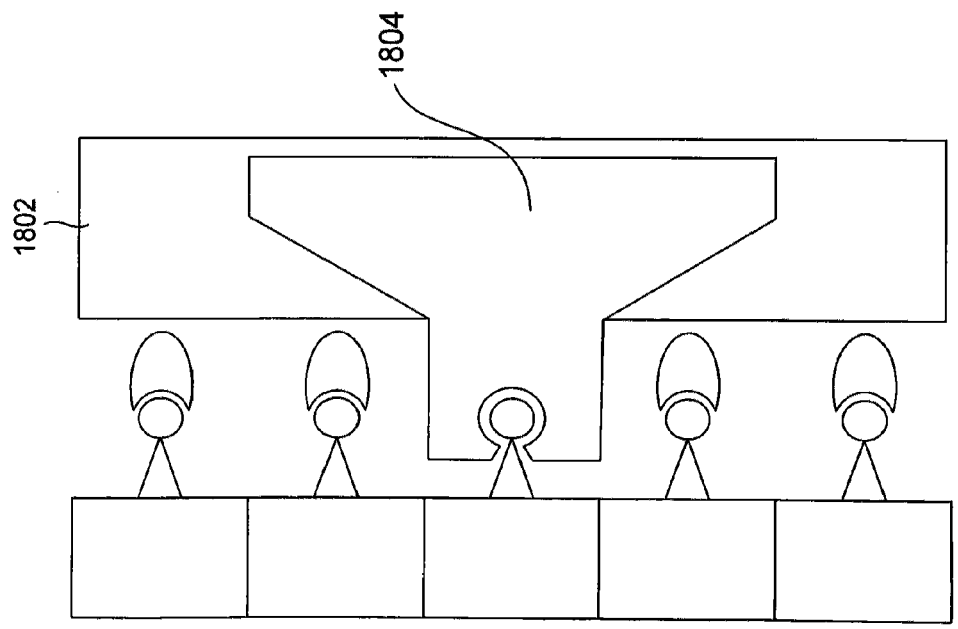
Figure 19:
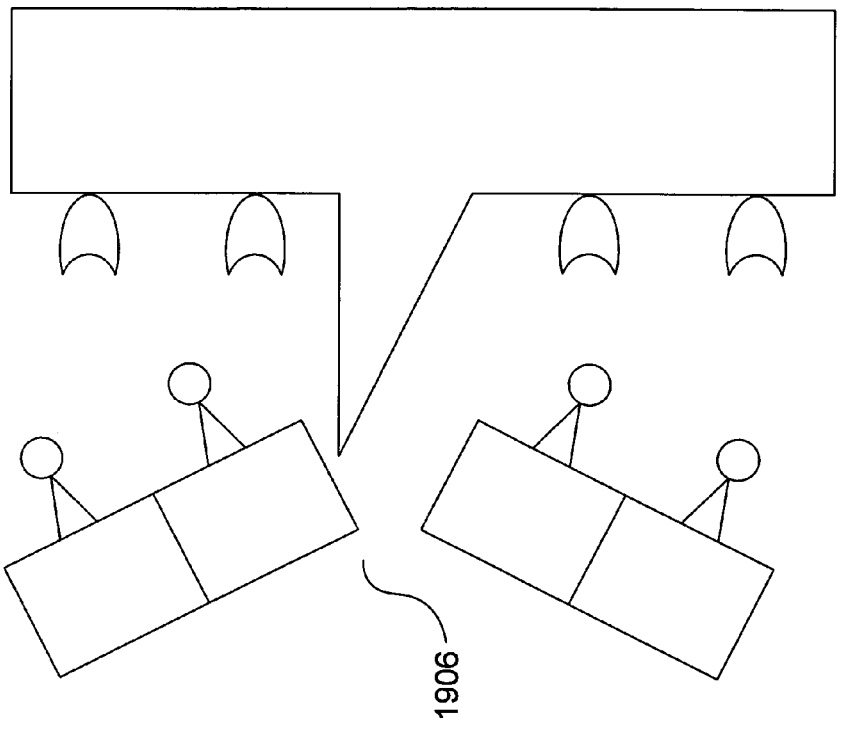
Figure 19:
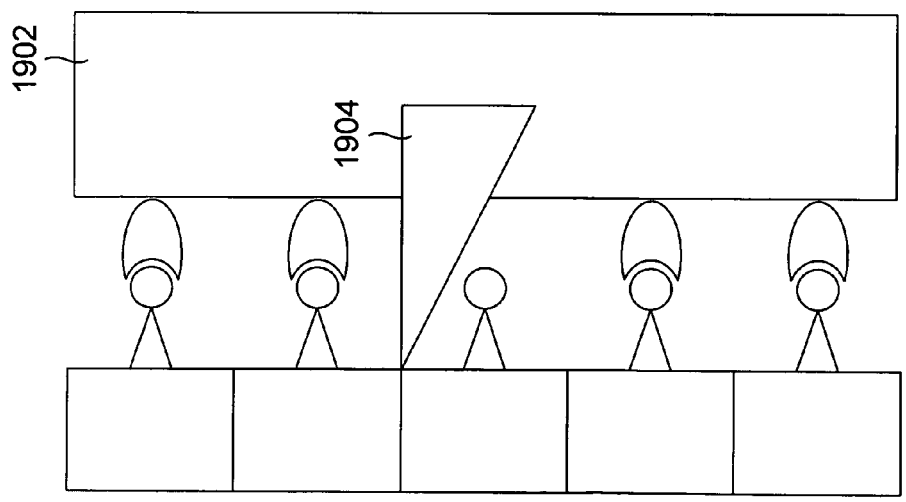
Figure 20:
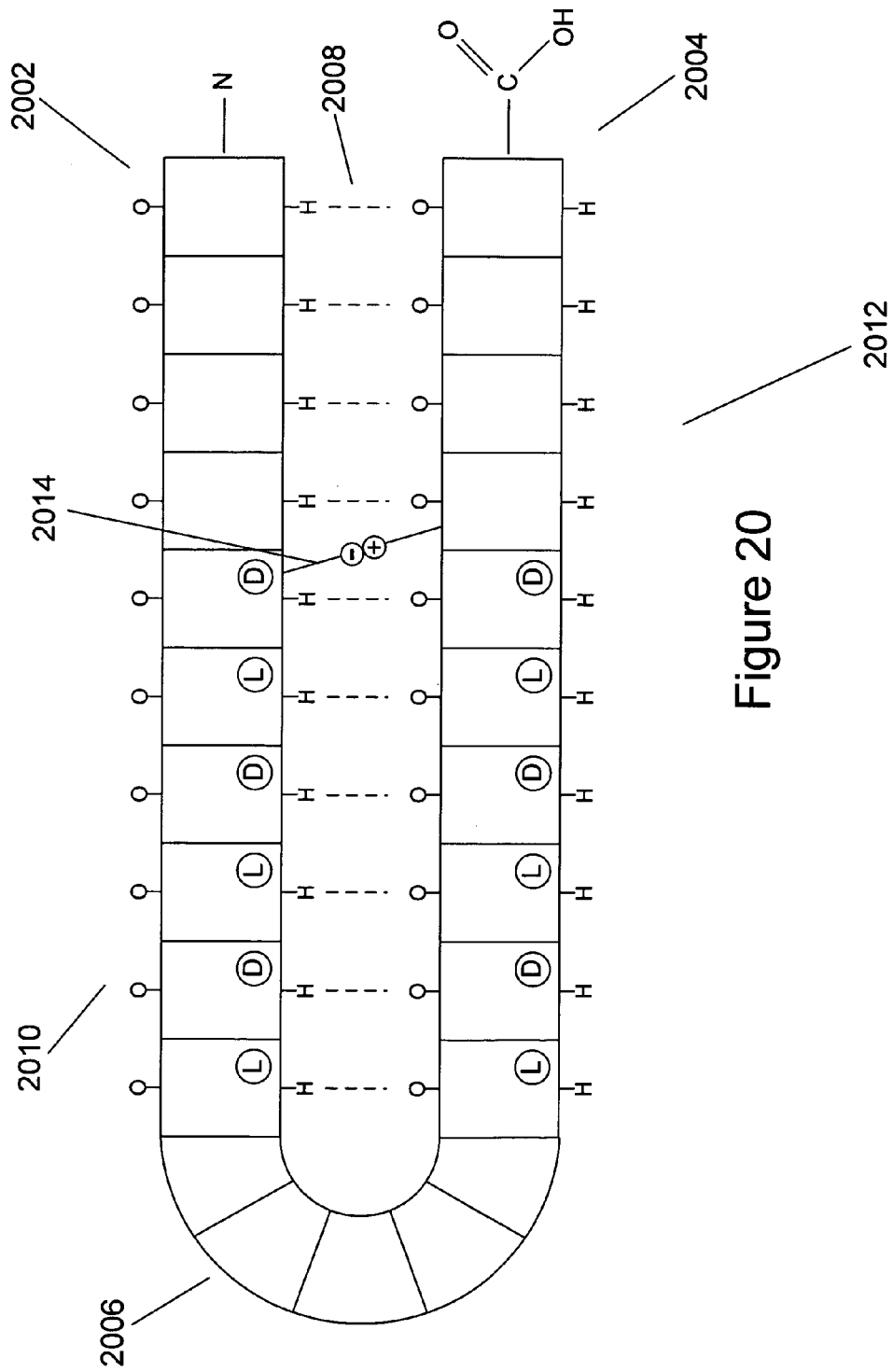
FIG. 20 shows a schematic diagram of a polypeptide therapeutic agent designed by computational methods to be complementary to, and bind to, extended-α-strand or α-sheet binding sites of amyloidogenic intermediates.
Figure 21:
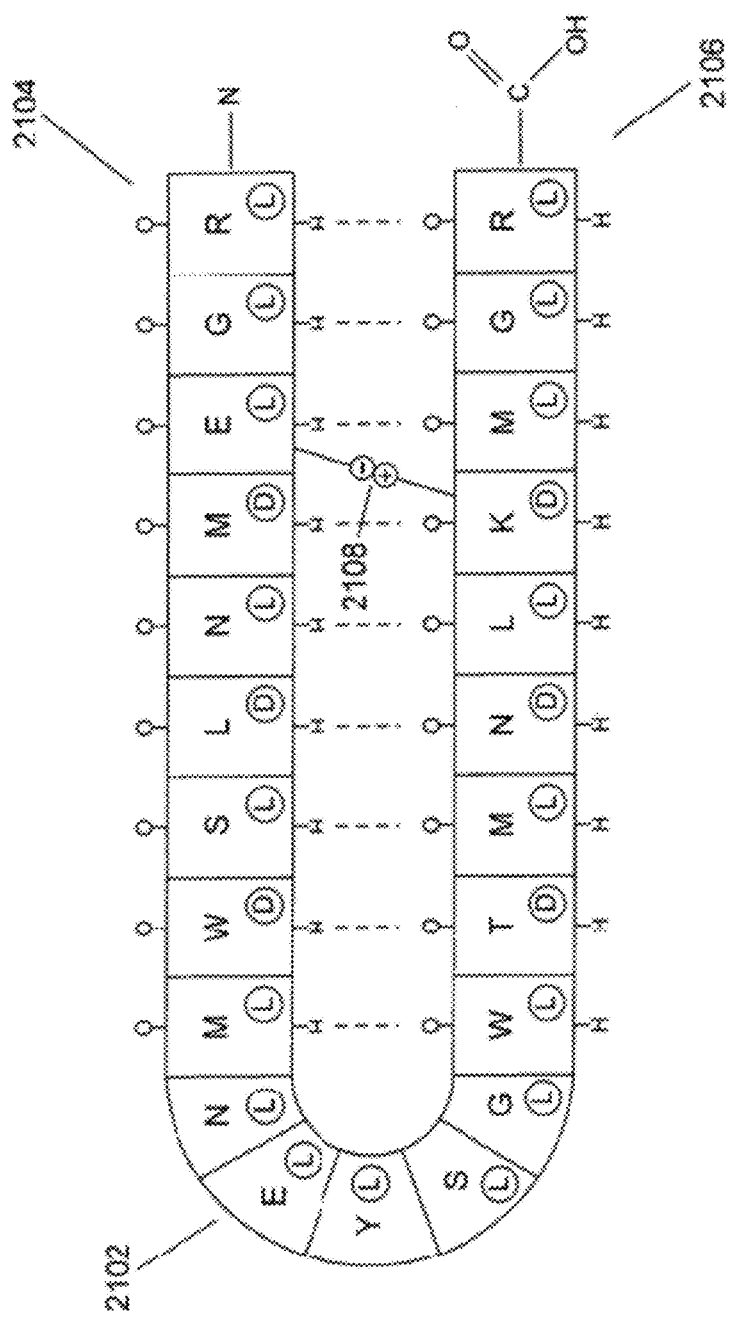
FIG. 21 illustrates one particular therapeutic polypeptide designed by computational techniques, to be described below.
Figure 22:
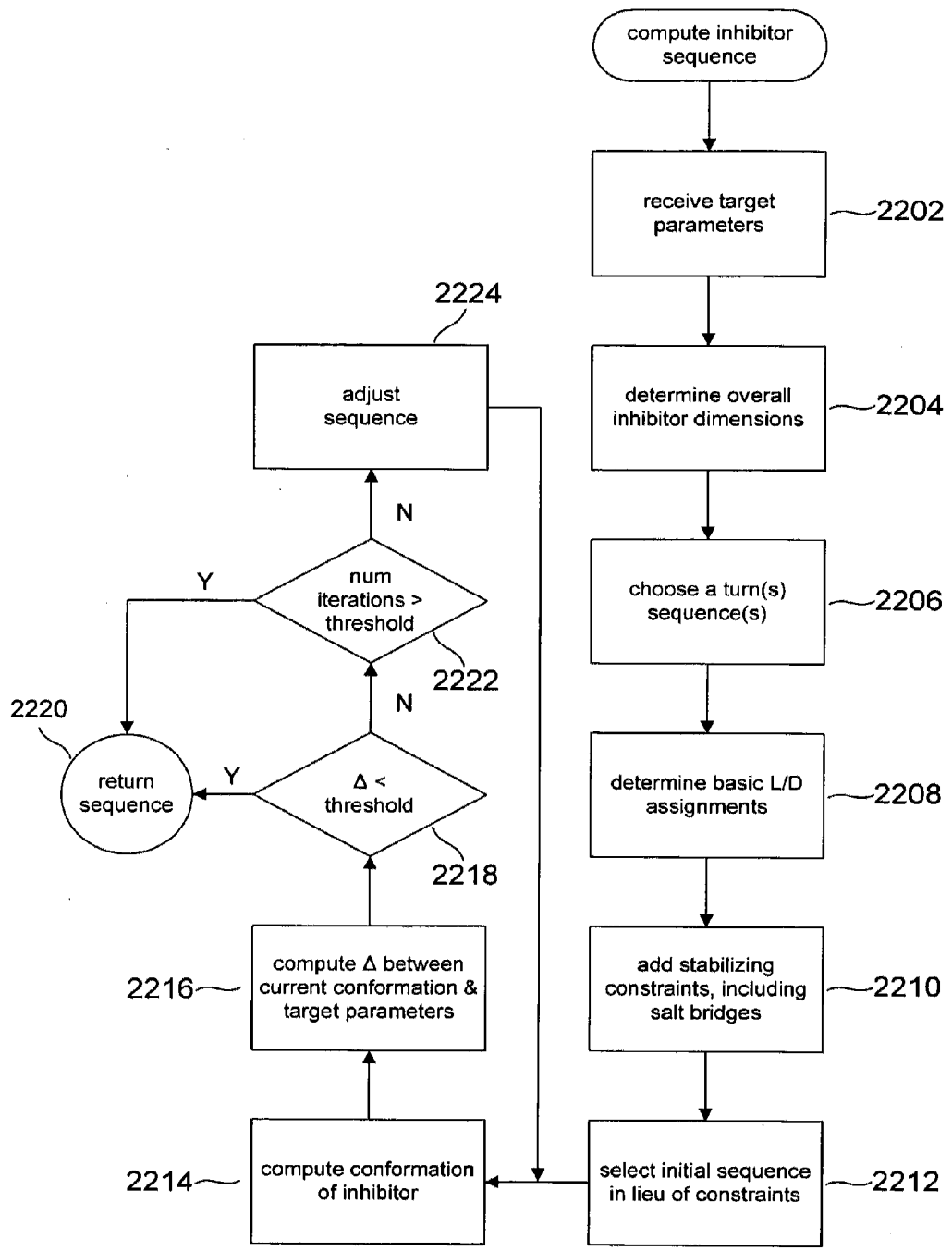
FIG. 22 is a simple control-flow diagram illustrating the computational methods by which polypeptide amyloidosis inhibitors, such as the polypeptide amyloidosis inhibitor shown in FIG. 21, can be designed.

FIG. 18 illustrates yet an additional scheme in which the therapeutic agent is designed to transfer a large chemical moiety to the extended α-strand or α-sheet secondary structure within a binding site of an amyloidogenic intermediate. As shown in FIG. 18, the therapeutic agent 1802 binds to the amyloidogenic-intermediate binding site via hydrogen bonding or electrostatic interactions and, additionally, transfers a large chemical moiety 1804 to the amyloidogenic-intermediate polypeptide strand. Presumably, the chemical moiety contains reactive groups that covalently bind to one or more atoms of the polypeptide. Subsequently, even were the therapeutic agent to dissociate from the binding site, the chemical moiety 1804 remains covalently bound to the binding site, blocking binding by complementary extended α-strand or α-sheet binding sites of other amyloidogenic intermediates and possibly directing protein-destruction machinery or an immune response to target the modified amyloidogenic-intermediate.

FIG. 19 provides yet an additional scheme for design of therapeutic molecules. As shown in FIG. 19, the therapeutic agent 1902 may include a reactive constituent or catalytic site 1904 that, once bound proximally to the extended α-strand or α-sheet binding site of an amyloidogenic intermediate, catalytically cleaves the polypeptide backbone 1906 and breaks the amyloidogenic intermediate into non-amyloidogenic fragments.

Many different possible therapeutic agents may be designed to target extended α-strand or α-sheet binding sites in amyloidogenic intermediates. It is possible that small-molecule or organometallic compounds that recognize the zigzag-like arrangement of carbonyl oxygens or amide hydrogens may be developed to tightly bind to the amyloidogenic-intermediate binding sites and thus prevent aggregation. Synthetic polypeptides and peptidomimetic compounds may be designed to exhibit extended-α-strand or α-sheet secondary structure and thus provide complementary edges for binding to the binding sites of amyloidogenic intermediates. Other biopolymers, including nucleic-acid biopolymers, glycoproteins, and even polysaccharides may be designed to recognize and bind to exposed α-strand or α-sheet edges. Various types of biopolymers and small-molecule therapeutic agents can be designed by computational drug-design methods to target the well-characterized extended α-strand or α-sheet carbonyl-oxygen and amide-hydrogen-rich edges.

One Therapeutic-Agent Embodiment of the Present Invention

FIG. 20 shows a schematic diagram of a polypeptide therapeutic agent designed by computational methods to be complementary to, and bind to, extended-α-strand or α-sheet binding sites of amyloidogenic intermediates. The polypeptide includes two extended-α-strand arms 2002 and 2004 joined together by a sequence of amino-acid monomers that are conformationally disposed to create a bend or hairpin-like turn 2006 so that the two extended α-strand arms 2002 and 2004 are adjacent to one another, in anti-parallel fashion to allow for α-sheet hydrogen bonding 2008 that holds the entire synthetic polypeptide in a two-strand α-sheet conformation. In order to facilitate an α-sheet conformation, the amino-acid monomers within the extended α-strand arms alternate between L and D stereoisomers. L stereoisomers tend to adopt $\alpha_R$-conducive conformations, while D stereoisomers tend to adopt $\alpha_L$-conducive conformations. Thus, by alternating L and D stereoisomers, the amino-acid monomers are conformationally disposed towards the alternating $\alpha_L$ and $\alpha_R$ domains characteristic of the α-sheet secondary structure. The therapeutic polypeptide exhibits both an exposed carbonyl-oxygen-rich extended α-strand edge 2010 and an exposed amide-hydrogen-rich extended α-strand edge 2012, either or both of which may bind to docking sites of amyloidogenic intermediates. In addition to hydrogen bonding, the two extended α-strand arms 2002 and 2004 can be held together by salt bridges 2014 or other types of electrostatic interactions, or even by covalent bonds, between side chains of the amino-acid monomers of the extended α-strand arms.

FIG. 21 illustrates one particular therapeutic polypeptide designed by computational techniques, to be described below. The polypeptide includes five L-amino-acid monomers that form a hairpin turn 2102 and two extended-α-strand arms 2104 and 2106. In FIG. 21, the single-character abbreviations for the amino-acid monomers are shown, as well as circle indications of the stereoisometric form of each amino-acid monomer. A salt bridge 2108 comprising large side chains of the glutamic acid and lysine monomers is intentionally included to further stabilize the α-sheet secondary structure of the synthetic polypeptide. While the polypeptide shown in FIG. 21 is one candidate therapeutic agent for preventing or ameliorating $PrP^{SC}$ aggregation and for potentially for binding to, and facilitating clearance of soluble $PrP^{SC}$ amyloidogenic intermediates from an organism, many other, similar polypeptide and peptidomimetic compounds can be constructed, by computational design methodology, to serve as inhibitors of amyloidosis. For example, the extended α-strand and α-sheet secondary structure within a polypeptide or peptidomimetic inhibitor may feature additional conformation, such as curling or rolling of the α-sheet over longer-range distances. Such additional conformational features may result in various types of long-range curvature of the zigzag-like carbonyl-oxygen-rich and amide-hydrogen-rich edges. Computational design methods may be employed to alter the sequence of amino-acid monomers, alter the pattern of D and L stereoisomers within the inhibitor, and add additional features, such as additional salt bridges or even covalent bonds between amino-acid-monomer side chains, in order to achieve the conformation complementary to the binding sites of particular amyloidogenic intermediates.

FIG. 22 is a simple control-flow diagram illustrating the computational methods by which polypeptide amyloidosis inhibitors, such as the polypeptide amyloidosis inhibitor shown in FIG. 21, can be designed. In step 2202, parameters for the particular target binding site are received. These parameters may include the type of edge, either carbonyl-oxygen-rich or amide-hydrogen-rich, the length of the binding region, any additional conformational parameters, such as additional curvature, and any conformational constraints exhibited by the surface of the amyloidogenic intermediate near the binding site. Next, in step 2204, the overall dimension and conformation of a desired polypeptide inhibitor is determined by determining an initial structure that is complementary to the target binding site. Next, in step 2206, a short stretch of amino-acid monomers disposed towards forming a bend or hairpin turn, such as hairpin turn 2102 in FIG. 21, are selected. Once the turn sequence is selected, then, in step 2208, the stereoisomer assignments, L or D, are determined for the amino-acid residues in the extended α-strand arms of the inhibitor. Next, in step 2210, any additional stabilizing features, such as salt bridges, inter-arm covalent linkages, aromatic stacking or hydrophobic interactions of side chains, and other stabilizing features may be added by selecting appropriate amino-acid monomers for particular positions in the extended α-strand arms. In step 2212, an initial sequence of amino-acid monomers is chosen for the two extended α-strand arms of the inhibitor. The initial sequence can be computationally selected by applying the various conformational and dimensional constraints determined in step 2204 and carrying out a directed state search of possible sequences or, alternatively, by carrying out sequence optimization with a goal of producing the specified conformation. In step 2214, any of numerous different conformation-prediction algorithms can be applied to compute an initial conformation of the polypeptide sequence determined in step 2212. Then, in step 2216, the difference between the computed conformation and the desired conformation is computed. Any of various difference metrics can be applied in this step, including computing a root-mean-square ("RMS") deviation between backbone carbonyl oxygens or amide hydrogens and the desired arrangement of the carbonyl oxygens or amide hydrogens. When the computed difference is less than some threshold value, as determined in step 2218, then the current sequence is returned in step 2220. Otherwise, when the number of iterations of the loop comprising steps 2214, 2216, 2218, 2222, and 2224 has exceeded a second threshold, as determined in step 2222, the current sequence is returned. Otherwise, in step 2224, the current sequence is adjusted computationally in order to produce a conformation closer to the desired conformation, either by using an optimization approach, such as computing a steepest descent trajectory toward the desired conformation, or by other approaches. Following sequence adjustment, control is returned in step 2214 for another iteration of difference computation and sequence adjustment.

Exemplary Targets and Synthetic-Peptide Inhibitors

Figure 23:
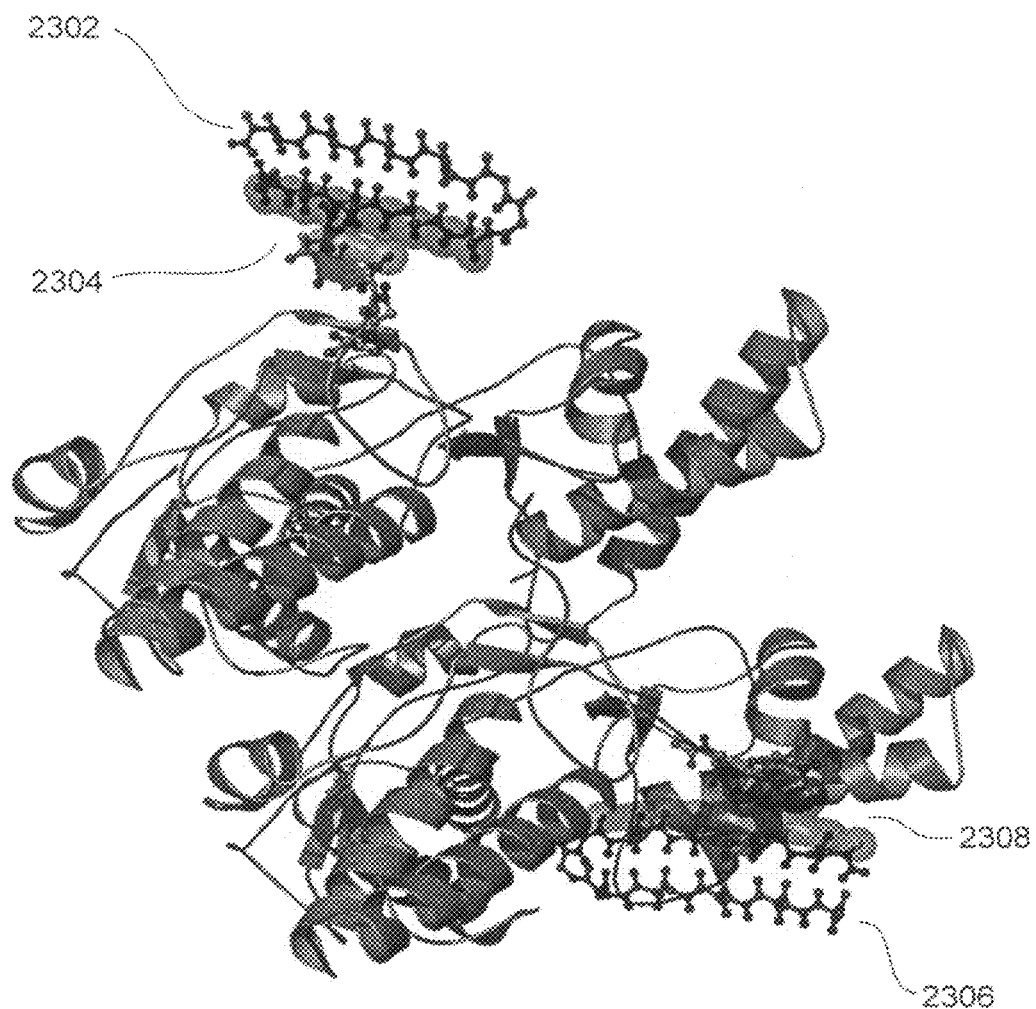
FIG. 23 shows a molecular model of the $PrP^{SC}$ amyloidogenic intermediate generated by partial unfolding and refolding of the prion protein $PrP^C$, and two synthetic polypeptide inhibitors bound to binding sites exhibited by the $PrP^{SC}$ amyloidogenic intermediate.
Figure 24:
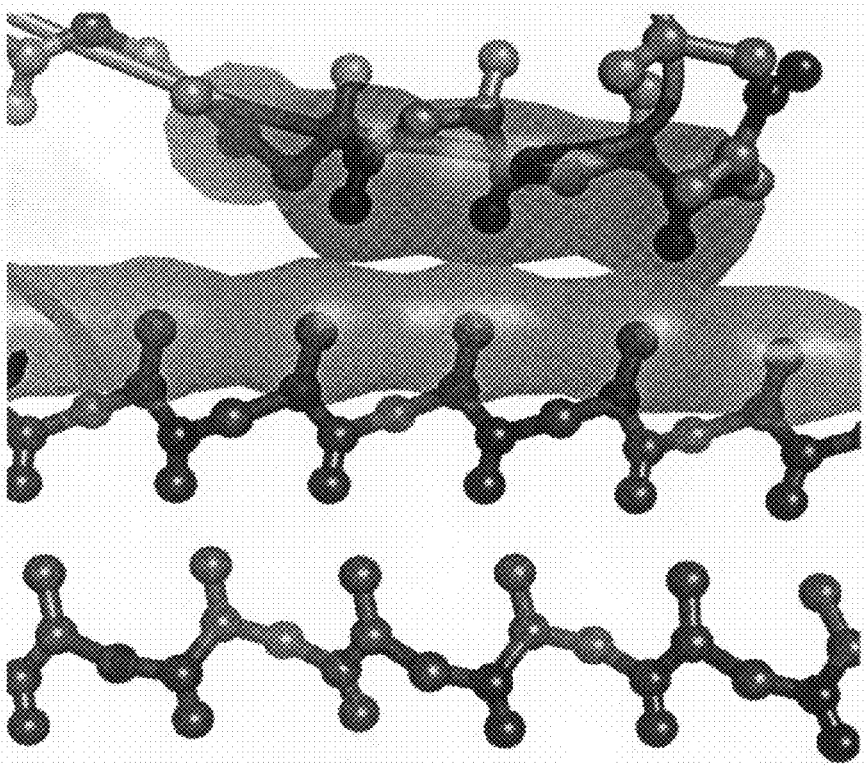
FIG. 24 provides close-up detail of the synthetic inhibitor of FIG. 23 bound to the (+) binding site.
Figure 25:
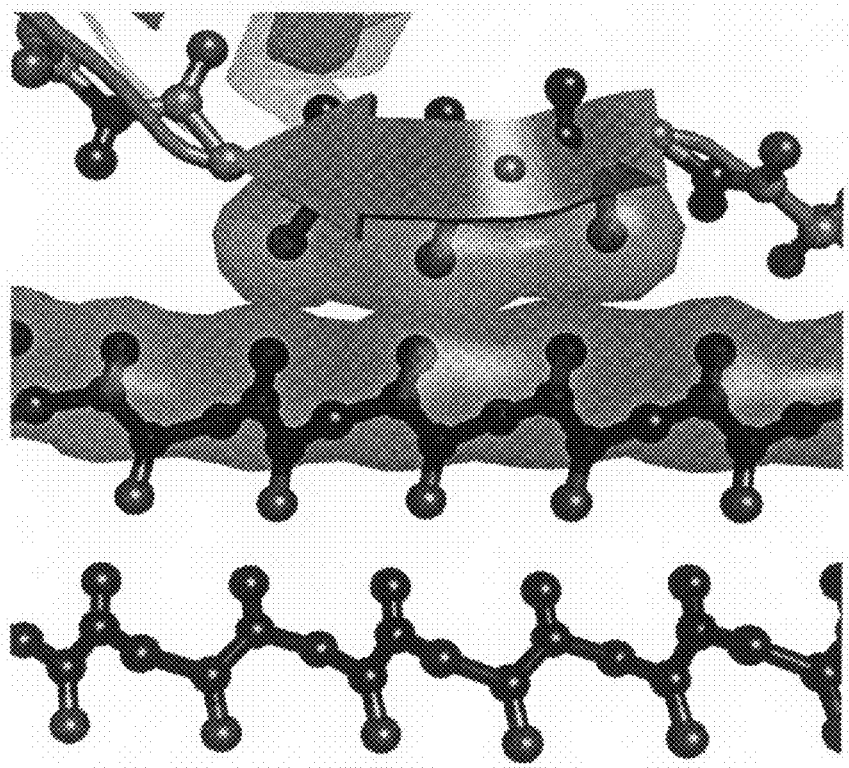
FIG. 25 shows close-up detail of the synthetic inhibitor of FIG. 23 bound to the (−) binding site.
Figure 26:
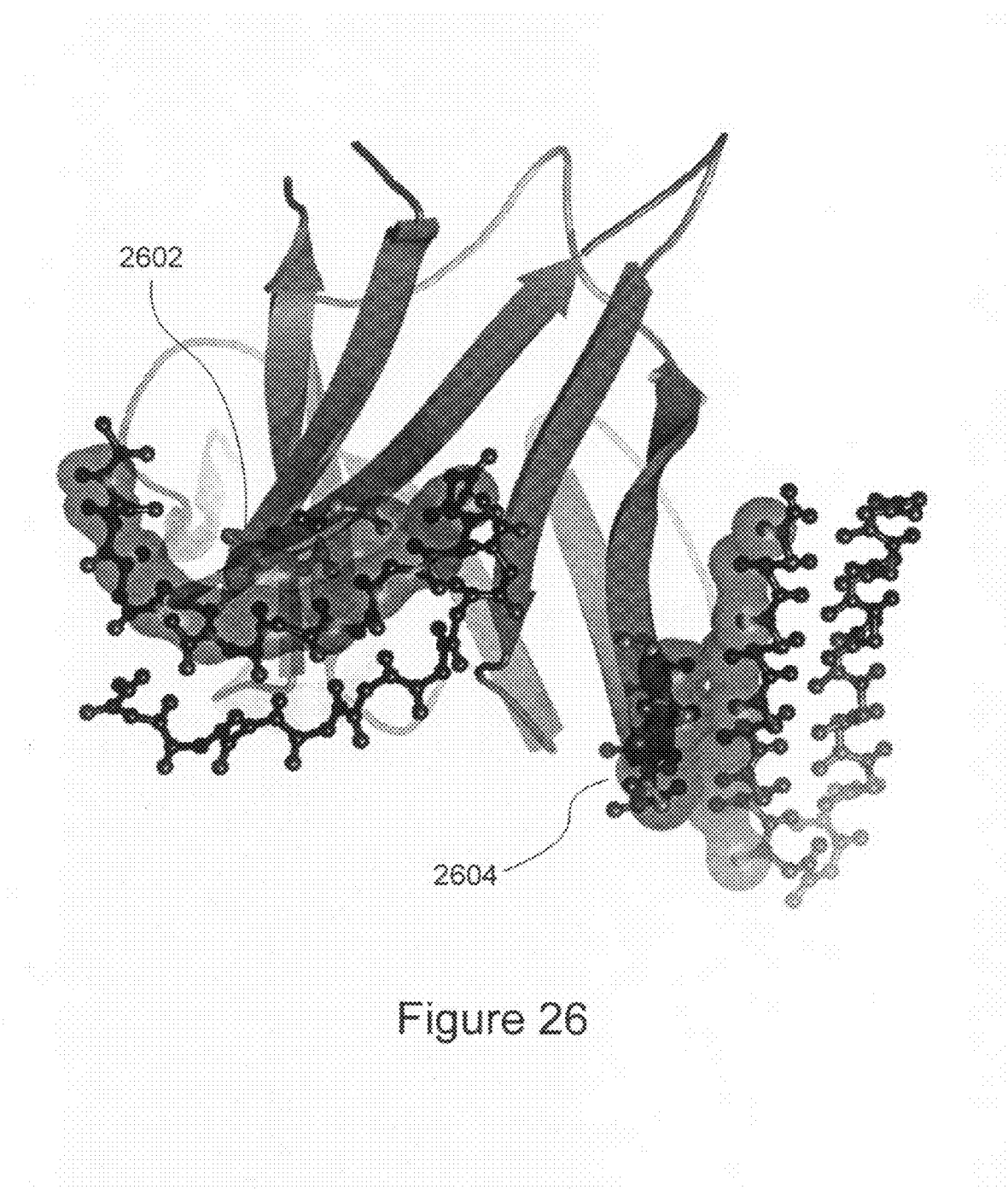
FIG. 26 shows a molecular model of the superoxide dismutase amyloidogenic intermediate and two synthetic polypeptide inhibitors bound to binding sites exhibited by the superoxide dismutase amyloidogenic intermediate.
Figure 27:
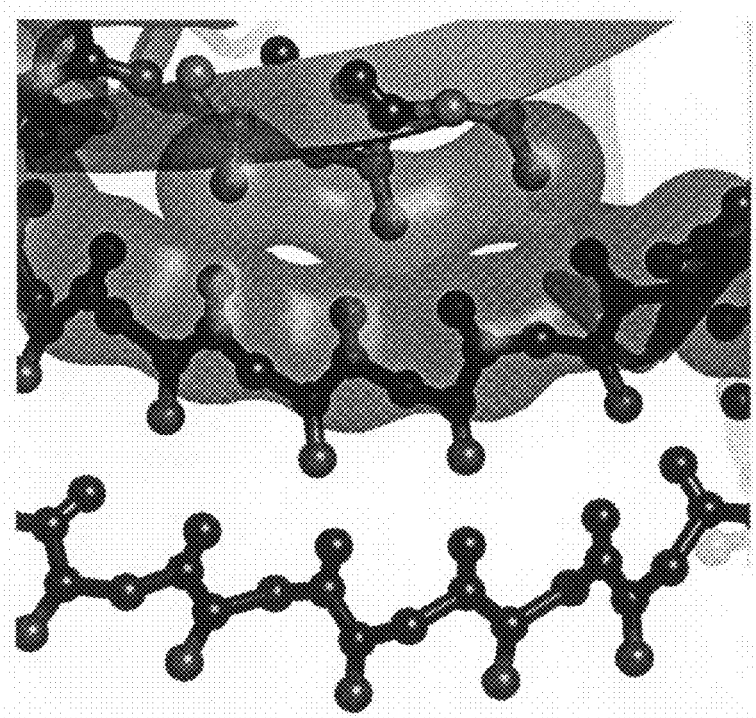
FIG. 27 provides close-up detail of the synthetic inhibitor of FIG. 26 bound to the (−) binding site.
Figure 28:
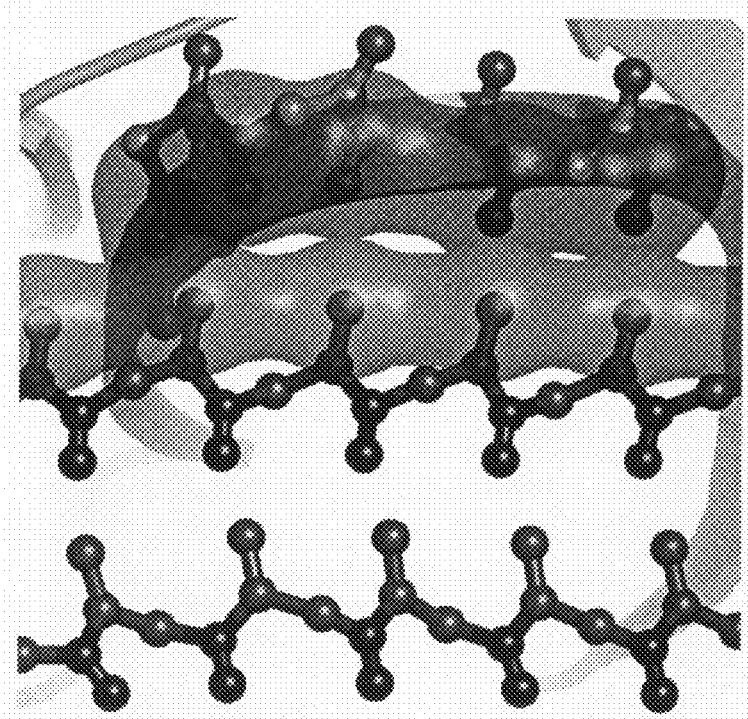
FIG. 28 provides close-up detail of the synthetic inhibitor of FIG. 26 bound to the (+) binding site.

FIG. 23 shows a molecular model of the PrP$^{SC}$ amyloidogenic intermediate generated by partial unfolding and refolding of the prion protein PrP$^C$, and two synthetic polypeptide inhibitors bound to binding sites exhibited by the PrP$^{SC}$ amyloidogenic intermediate. A first synthetic peptide inhibitor 2302 is bound to a (−) binding site 2304 and a second polypeptide inhibitor 2306 is bound to a (+) binding site 2308. FIG. 24 provides close-up detail of the synthetic inhibitor of FIG. 23 bound to the (+) binding site. FIG. 25 shows close-up detail of the synthetic inhibitor of FIG. 23 bound to the (−) binding site. FIG. 26 shows a molecular model of the superoxide dismutase amyloidogenic intermediate and two synthetic polypeptide inhibitors bound to binding sites exhibited by the superoxide dismutase amyloidogenic intermediate. The superoxide dismutase amyloidogenic intermediate includes a (−) binding site 2602 and a (+) binding site 2604. FIG. 27 provides close-up detail of the synthetic inhibitor of FIG. 26 bound to the (−) binding site. FIG. 28 provides close-up detail of the synthetic inhibitor of FIG. 26 bound to the (+) binding site.

Although the present invention has been described in terms of particular embodiments, it is not intended that the invention be limited to these embodiments. Modifications within the spirit of the invention will be apparent to those skilled in the art. For example, as discussed above, any of a variety of different types of biopolymers, small-molecule compounds, and other compounds can be computationally designed to recognize and bind to the carbonyl-oxygen-rich and/or amide-hydrogen-rich edge regions of extended-α-strand and α-sheet secondary structure within amyloidogenic intermediates. Synthetic peptides, peptidomimetic compounds, RNA, and other types of biopolymers may be designed to provide a complementary binding region, with complementarity mediated by weakly acidic or weakly basic substituent groups that are arranged in a proper geometry to form hydrogen bonds with extended α-strand edges, or by substituent groups having complementary localized dipole moments and complementary overall dipole moments to bind electrostatically to the extended α-strand binding sites of amyloidogenic intermediates. In addition, therapeutic inhibitors may be supplemented with additional, chemically reactive groups that can transfer chemical groups to the amyloidogenic intermediates, covalently bond to the amyloidogenic intermediates, and catalytically cleave amyloidogenic intermediates. Molecular-dynamics-based computational therapeutic-design methods can be programmed in numerous different programming languages for execution on a variety of different hardware and software platforms, and many different alternative implementations can be obtained by changing the well-known and familiar programming parameters, including modular organization, control structures, data structures, and variables, and by use of different pre-existing library routines and programs. Because the extended-α-strand or α-sheet secondary structure appears to be a common motif in all of the currently known amyloidogenic intermediates, it is reasonable to expect that therapeutic small-molecule compounds may have benefit in treating and preventing a variety of different amyloid diseases.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A polypeptide comprising the amino acid sequence comprises $R_L G_L E_L M_D N_L L_D S_L W_D M_L N_L E_L Y_L S_L G_L W_L T_D M_L N_D L_L K_D M_L G_L R_L$ (SEQ ID NO.1), or a salt thereof, wherein "L" is an L-isomer of the recited amino acid sequence, and "D" is a D-isomer of the recited amino acid sequence.

2. The polypeptide of claim 1, comprising a salt bridge formed between the first E residue in the recited amino acid sequence and the K residue in the recited amino acid sequence.

3. The polypeptide of claim 1, wherein the polypeptide consists of the amino acid sequence $R_L G_L E_L M_D N_L L_D S_L W_D M_L N_L E_L Y_L S_L G_L W_L T_D M_L N_D L_L K_D M_L G_L R_L$ (SEQ ID NO.1), or a salt thereof.

4. The polypeptide of claim 2, wherein the polypeptide consists of the amino acid sequence $R_L G_L E_L M_D N_L L_D S_L W_D M_L N_L E_L Y_L S_L G_L W_L T_D M_L N_D L_L K_D M_L G_L R_L$ (SEQ ID NO.1), or a salt thereof.

* * * * *